United States Patent [19]
Sperl et al.

[11] Patent Number: 6,063,818
[45] Date of Patent: *May 16, 2000

[54] SUBSTITUTED BENZYLIDENE INDENYL FORMAMIDES, ACETAMIDES AND PROPIONAMIDES

[75] Inventors: Gerhard Sperl; Paul Gross, both of Stockton, Calif.; Klaus Brendel, Tucson, Ariz.; Rifat Pamukcu, Spring House; Gary A. Piazza, Doylestown, both of Pa.

[73] Assignee: Cell Pathways Inc., Horsham, Pa.

[*] Notice: This patent is subject to a terminal disclaimer.

[21] Appl. No.: 08/868,182

[22] Filed: Jun. 3, 1997

Related U.S. Application Data

[63] Continuation of application No. 08/661,293, Jun. 13, 1996.
[51] Int. Cl.[7] .................................................. A61K 31/165
[52] U.S. Cl. ........................ 514/622; 514/617; 514/618; 514/619
[58] Field of Search ...................... 514/617, 618, 514/619, 622

[56] References Cited

U.S. PATENT DOCUMENTS

| | | | |
|---|---|---|---|
| 3,161,654 | 12/1964 | Shen | 260/319 |
| 3,312,730 | 4/1967 | Winter et al. | 260/473 |
| 3,325,358 | 6/1967 | Winter et al. | 167/65 |
| 3,532,752 | 10/1970 | Shen | 260/570.8 |
| 3,609,184 | 9/1971 | Miyai et al. | 260/520 |
| 3,622,623 | 11/1971 | Shen et al. | 260/515 |
| 3,631,167 | 12/1971 | Shen et al. | 260/240 D |
| 3,642,785 | 2/1972 | Shen et al. | 260/240 R |
| 3,647,858 | 3/1972 | Hinkley et al. | 260/470 |
| 3,654,349 | 4/1972 | Shen et al. | 260/515 M |
| 3,692,651 | 9/1972 | Sletzinger | 204/158 R |
| 3,692,825 | 9/1972 | Conn | 260/515 A |
| 3,700,730 | 10/1972 | Hinkley | 260/515 A |
| 3,737,455 | 6/1973 | Shen et al. | 260/520 |
| 3,759,987 | 9/1973 | Conn et al. | 260/515 A |
| 3,766,259 | 10/1973 | Sletzinger | 260/515 A |
| 3,772,282 | 11/1973 | Ford, Jr. | 260/240 R |
| 3,812,109 | 5/1974 | Shen et al. | 260/240 R |
| 3,812,180 | 5/1974 | Shen et al. | 260/515 A |
| 3,822,310 | 7/1974 | Shen et al. | 260/515 A |
| 3,851,063 | 11/1974 | Shen et al. | 424/303 |
| 3,860,636 | 1/1975 | Shen et al. | 260/502.4 R |
| 3,860,659 | 1/1975 | Hinkley et al. | 568/37 |
| 3,868,414 | 2/1975 | Shen et al. | 260/515 A |
| 3,868,415 | 2/1975 | Jones | 260/515 A |
| 3,869,507 | 3/1975 | Jones | 260/515 A |
| 3,870,753 | 3/1975 | Tull et al. | 260/515 A |
| 3,888,902 | 6/1975 | Shen et al. | 260/465 D |
| 3,897,487 | 7/1975 | Jones | 260/515 A |
| 3,932,498 | 1/1976 | Shen et al. | 260/515 A |
| 3,944,600 | 3/1976 | Tull et al. | 260/515 A |
| 3,954,852 | 5/1976 | Shen et al. | 260/515 A |
| 3,956,363 | 5/1976 | Shen et al. | 260/479 A |
| 3,970,693 | 7/1976 | Tull et al. | 260/515 A |
| 3,998,875 | 12/1976 | Tull et al. | 260/515 A |
| 4,207,340 | 6/1980 | Gardocki | 424/317 |
| 4,233,457 | 11/1980 | Czaja et al. | 562/428 |
| 4,307,114 | 12/1981 | Dvornik et al. | 424/317 |
| 4,402,979 | 9/1983 | Shen et al. | 424/317 |
| 4,423,074 | 12/1983 | Dvornik et al. | 424/317 |
| 4,423,075 | 12/1983 | Dvornik et al. | 424/317 |
| 4,656,190 | 4/1987 | Shen et al. | 514/529 |
| 4,748,271 | 5/1988 | Meneghin | 562/428 |
| 4,943,587 | 7/1990 | Cetenko et al. | 514/415 |
| 5,112,868 | 5/1992 | Cetenko et al. | 514/618 |
| 5,229,516 | 7/1993 | Musser et al. | 546/172 |
| 5,401,774 | 3/1995 | Pamukcu et al. | 514/569 |
| 5,420,289 | 5/1995 | Musser et al. | 548/159 |
| 5,643,959 | 7/1997 | Pamukcu et al. | 514/569 |

FOREIGN PATENT DOCUMENTS

| | | |
|---|---|---|
| 61-106521 | 5/1986 | Japan . |
| 1178658 | 1/1970 | United Kingdom . |
| 91/06537 | 5/1991 | WIPO . |
| 96/03120 | 2/1996 | WIPO . |
| 96/03987 | 2/1996 | WIPO . |

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

*Primary Examiner*—Richard L. Raymond
*Attorney, Agent, or Firm*—Robert W. Stevenson

[57] ABSTRACT

Substituted benzylidene indenyl formamides, acetamides and propionamides are useful in the treatment of precancerous lesions and neoplasms.

47 Claims, No Drawings

SUBSTITUTED BENZYLIDENE INDENYL FORMAMIDES, ACETAMIDES AND PROPIONAMIDES

This application is a continuation of U.S. patent application Ser. No. 08/661,293, filed Jun. 13, 1996.

TECHNICAL FIELD

This invention relates to compounds and methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e., the cases of so-called common sporadic polyps), polyp removal will be effective to reduce the risk of cancer. In a small percentage of cases (i.e., the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g., hundreds or more) of polyps—literally covering the colon in some cases—making safe removal of the polyps impossible short of surgical removal of the colon.

Because each polyp carries with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those with high risk genetic factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs.

Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

In the last few years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations and ulcerations, Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reported to be converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes both pharmaceutical compositions containing compounds and a method of treating patients with precancerous lesions by administering a pharmacologically effective amount of those compounds described below to a patient in need of such treatment. Such compositions are effective in modulating apoptosis and eliminating and inhibiting the growth of precancerous lesions and neoplasms, but are not characterized by the severe side reactions of conventional NSAIDs.

The compounds used in the treatment of this invention are believed to be effective on precancerous lesions either because they are active themselves or because they are metabolized to active derivatives.

It was unexpectedly discovered that while the compounds of this invention do not greatly inhibit prostaglandin synthesis—prostaglandin synthesis inhibition being a characteristic of conventional NSAIDs—the compounds of this invention nonetheless have antiproliferative effects on precancerous lesion cells.

DETAILED DESCRIPTION OF THE INVENTION

As discussed above, the present invention provides a pharmaceutical composition that includes compounds of formula I below for treating a patient with precancerous lesions:

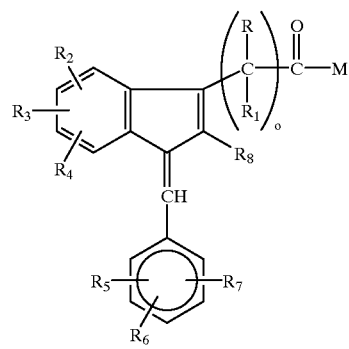

wherein R and $R_1$ are independently selected from the group consisting of hydrogen, hydroxy, lower alkyl and amino; or R and $R_1$ together may be oxygen, $R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are identically selected from the group consisting of hydroxy and lower alkoxy, and the third is selected from the group consisting of hydroxy, halogen, lower alkoxy, lower alkyl, amino and lower dialkylamino, with the proviso that when at least one of $R_2$, $R_3$ or $R_4$ is lower alkoxy, then each of $R_5$, $R_6$ and $R_7$ are hydroxy or lower alkoxy;

$R_8$ is selected from the group consisting of hydrogen and lower alkyl;

o may be 0, 1 or 2; and

M is selected from the group consisting of amino, alkylamino, dialkylamino, alkoxyamino, alkenylamino, alkynylamino, hydroxyalkylamino, polyhydroxyalkylamino, dialkylaminoalkylamino, aminoalkylamino, arylalkylamino selected from the group consisting of benzylamino, anilino and phenylalkylamino, aminoindan, and heterocycloalkylamino where the heterocycles are selected from the group consisting of pyridinyl, piperidinyl, piperazinyl, pyrrollidinyl and N-morpholino; wherein the alkyl between the cyclic structure and the amino may be absent, and the cyclic structures may optionally be substituted with one or more of halo, alkoxy, hydroxy, amino, alkylamino, dialkylamino and sulfonamido; or M may be NR'R" where NR' is as described above and R" is selected from alkyl, cyanoalkyl, haloalkyl, alkylamino, dialkylaminoalkyl, alkanoylalkylester and pyridinyl.

Preferably, o is 1 or 2; and M is selected from the group consisting of amino, alkylamino, dialkylamino, alkenylamino, alkynylamino, hydroxyalkylamino, dialkylaminoalkylamino, arylalkylamino selected from the group consisting of benzylamino, anilino and phenylalkylamino, aminoindan, and heterocycloalkylamino where the heterocycles are selected from the group consisting of pyridinyl, piperidinyl, piperazinyl, and pyrrollidinyl; wherein the alkyl between the cyclic structure and the amino may be absent, and the cyclic structures may optionally be substituted with one or more of halo, alkoxy, hydroxy, amino, alkylamino and dialkylamino; or M may be NR'R" where NR' is as described above and R" is selected from alkyl, cyanoalkyl, alkylamino, dialkylaminoalkyl and alkanoylalkylester.

More preferably, M is selected from the group consisting of alkenylamino, alkynylamino, benzylamino, and pyridinylalkylamino, wherein the cyclic structures may optionally be substituted with one or more of halo, alkoxy, hydroxy, amino, alkylamino and dialkylamino; or M may be NR'R" where NR' is as described above and R" is selected from alkyl, alkylamino and dialkylaminoalkyl.

Even more preferably, M is selected from the group consisting of alkenylamino, alkynylamino, benzylamino, and pyridinylalkylamino, wherein the cyclic structures may optionally be substituted with one or more of halo, alkoxy, hydroxy, amino, alkylamino and dialkylamino.

Still more preferably, M is selected from benzylamino and benzylamino substituted with one or more of halo, alkoxy, hydroxy, amino, alkylamino and dialkylamino. Yet still more preferably, M is selected from the group consisting of benzylamino and benzylamino substituted with one or more of halo, alkoxy and hydroxy. Most preferably, M is benzylamino.

For other substituents of the compound of formula I, when M is at least in its even more preferred form, preferably, R and $R_1$ are independently selected from the group consisting of hydrogen and hydroxy; at least two of $R_5$, $R_6$ and $R_7$ are lower alkoxy and the third is selected from hydroxy, lower alkoxy, amino and lower dialkylamino; or each of $R_5$, $R_6$ and $R_7$ are hydroxy.

More preferably, R and $R_1$ are hydrogen; $R_2$, $R_3$ and $R_4$ are independently selected from the group consisting of hydrogen, hydroxy, halogen, lower alkoxy, lower alkyl and alkyl mercapto; at least two of $R_5$, $R_6$ and $R_7$ are lower alkoxy and the third is selected from hydroxy and lower alkoxy; $R_8$ is lower alkyl; and o is 1.

Even more preferably, $R_5$, $R_6$ and $R_7$ are each lower alkoxy; and $R_8$ is methyl.

Still more preferably, $R_2$ is selected from the group consisting of hydroxy, halogen, lower alkoxy and alkyl mercapto; $R_4$ is hydrogen; and $R_5$, $R_6$ and $R_7$ are each methoxy.

Yet still more preferably, $R_2$ is selected from the group consisting of hydroxy, halogen and lower alkoxy; and $R_3$ is hydrogen. Even still more preferably, $R_2$ is halogen, preferably fluoro.

A preferred group of compounds includes:
(Z)-5-Fluoro-2-methyl-1-(2,4,6-trimethoxybenzylidene)-3-(N-benzyl)-indenylacetamide,
(Z)-5-Fluoro-2-methyl-1-(3,4,5-trimethoxybenzylidene)-3-(N-benzyl)-indenylacetamide;
(E)-5-Fluoro-2-methyl-1-(3,4,5-trimethoxybenzylidene)-3-(N-benzyl)-indenylacetamide;
(Z)-5-Fluoro-2-methyl-1-(2,3,4-trimethoxybenzylidene)-3-(N-benzyl)-indenylacetamide; and
(Z)-5-Fluoro-2-methyl-1-(2,4,5-trimethoxybenzylidene)-3-(N-benzyl)-indenylacetamide.

Preferred compounds are (Z)-5-fluoro-2-methyl-1-(3,4,5-trimethoxybenzylidene)-3-(N-benzyl)-indenylacetamide and the corresponding E-isomer. The most preferred compound is (Z)-5-fluoro-2-methyl-1-(3,4,5-trimethoxybenzylidene)-3-(N-benzyl)-indenylacetamide.

The present invention also is a method of treating a patient with precancerous lesions by administering to a patient a pharmacologically effective amount of a pharmaceutical composition that includes a compound of formula I, wherein $R_1$ through $R_8$ are as defined above. Preferably, this composition is administered without therapeutic amounts of an NSAID.

The present invention is also a method of treating individuals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of formula I, wherein $R_1$ through $R_8$ are defined as above.

In still another form, the invention is a method of inducing apoptosis in human cells by exposing those cells to an effective amount of compounds of formula I, wherein $R_1$ through $R_8$ are defined as above where such cells are sensitive to these compounds.

Additionally, in yet another form, the invention is a method of treating a patient having a disease which would benefit from regulation of apoptosis by treating the patient with an effective amount of compounds of formula I, wherein $R_1$ through $R_8$ are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include adenomatous growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

Compounds of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of this invention excipients such as cocoa butter or a suppository wax.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

The foregoing may be better understood from the following examples, that are presented for purposes of illustration and are not intended to limit the scope of the invention. As used in the following examples, the references to substituents such as R, $R_1$, $R_2$, etc., refer to the corresponding compounds and substituents in the formula I above.

EXAMPLES

EXAMPLE 1

(Z)-5-fluoro-2-methyl-1-(3,4,5-trimethoxnbenzylidene)-3-(N-Benzyl)-indenylacetamide (A) p-Fluoro-α-methylcinnamic acid.

p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2 l of water. The aqueous solution is extracted with ether, and the ether extracts washed with potassium hydroxide solution. The combined aqueous layers are filtered, are acidified with concentrated HCl, and are filtered. The collected solid, p-fluoro-(X-methylcinnamic acid, is washed with water, and is dried and used as obtained.

(B) p-Fluoro-α-methylhydrocinnamic acid.

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the filtrate is concentrated in vacuo to give the product, p-fluoro-α-methylhydrocinnamic acid, which was used without weighing in the next step.

(C) 6-Fluoro-2-methylindanone

To 932 g polyphosphoric acid at 70° C. (on the steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and added to 2l. of water. The aqueous layer is extracted with ether, the ether solution is washed twice with saturated sodium chloride solution, 5% $Na_2CO_3$ solution, water, and is then dried. The ether filtrate is concentrated with 200 g silica-gel, and is added to a five pound silica-gel column packed with 5% ether-petroleum ether. The column is eluted with 5–10% ether-petroleum ether, to give 6-fluoro-2-methylindanone. Elution is followed by TLC.

(D) 5-fluoro-2-methylindenyl-3-acetic acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is concentrated, and the residue dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, 500 ml water added, the aqueous soluition is washed well with ether and then boiled with charcoal. The aqueous filtrate is acidified to pH 2 with 50% cold hydrochloric acid. The precipitate and dried 5-fluoro-2-methylindenyl-3-acetic acid (M.P. 164–166° C.) is obtained.

(E) (Z)-5-fluoro-2-methyl-1-(3,4,5-trimethoxybenzylidene)-3-indenylacetic acid 5-fluoro-2-methyl-3-indenylacetic acid (15 g, 0.072 mol), 3,4,5-trimethoxybenzaldehyde (17.85 g, 0.091 mol) and sodium methoxide (13.0 g, 0.24 mol) are heated in methanol (200 ml) at 60° C. under nitrogen with stirring for 6 hours. After cooling, the reaction mixture is poured into 750 ml of ice-water, and is acidified with 2.5 N hydrochloric acid. The collected solid is triturated with a little ether to produce (Z)-5-fluoro-2-methyl-1-(3,4,5-trimethoxybenzylidene)-3-indenylacetic acid (M .P. 166–169° C.).

(F) (Z)-5-fluoro-2-methyl-1-(3,4,5-trimethoxybenzylidene)-3-indenylacetyl chloride (Z)-5-fluoro-2-methyl-1-(3,4,5-trimethoxybenzylidene)-3-indenylaceticacid (20.64 g, 54.70 mmol) in THF (150 ml) is allowed to react with oxalylchloride (2 M in $CH_2Cl_2$; 35 ml; 70 mmol) under reflux conditions (24 h). The solvent is evaporated to yield the title compound, which is used as such in the next step.

(G) (Z)-5-fluoro-2-methyl-1-(3,4,5-trimethoxybenzylidene)-3-(N-benzyl)-indenylacetamide
Method I)

Benzylamine (0.55 ml, 5 mmol) is added slowly at room temperature to a solution of (Z)-5-fluoro-2-methyl-2-(3,4,5-trimethoxybenzylidene)-3-indenylacetyl chloride (step F, 1 g, 2.5 mmol) in $CH_2Cl_2$ (25 ml). The reaction mixture is refluxed overnight, and extracted with aqueous HCl (10%), water, and aqueous $NaHCO_3$ (5%). The organic phase is dried ($Na_2SO_4$) and is evaporated to give the yellow title compound, which is recrystallized from ethyl acetate to give the title compound (M.P. 191° C.).
(R=H, $R_1$=H, $R_2$=F, $R_3$=H, $R_4$=H, $R_5$=$OCH_3$, $R_6$=$OCH_3$, $R_7$=$OCH_3$, $R_8$=$CH_3$, o=1, M=$PhCH_2NH$)
Method II)

(Z)-5-fluoro-2-methyl-1-(3,4,5-trimethoxybenzylidene)-3-indenylacetic acid (1 g, 2.60 mmol) in DMA (5 ml) is allowed to react with N-(3-dimethylaminopropyl)-N'-ethylcarbodiimide hydrochloride (0.77 g, 4 mmol) and benzylamine (0.38 ml, 3.5 mmol) at room temperature for two days. The reaction mixture is added dropwise to stirred ice-water (400 ml). A yellow precipitate is filtered off, is washed with water (200 ml), and is dried in vacuo. Recrystallization from ethyl acetate gives the title compound.

Method III)

(Z)-5-fluoro-2-methylindene-3-(N-benzyl)-acetamide (1 g, 3.38 mmol), 3,4,5-trimethoxybenzaldehyde (0.74 g, 4 mmol), and sodium methoxide (30 ml, 1 M NaOCH$_3$ in methanol) are heated at 60° C. under nitrogen with stirring for 24 h. After cooling, the reaction mixture is poured into ice-water (200 ml). A yellow solid is filtered off, is washed with water (100 ml), and dried in vacuo. Recrystallization from ethyl acetate gives the title compound.

EXAMPLES 2–51

When the methods for example 1(G) are followed but substituting for benzylamine each of the amines listed in Table 1, there are obtained the corresponding amides listed in Table 2.

TABLE 1

| Example | Amine |
| --- | --- |
| 2 | 3-iodobenzylamine |
| 3 | 3-chlorobenzylamine |
| 4 | 2-chlorobenzylamine |
| 5 | 3,4-dichlorobenzylamine |
| 6 | 2,4-difluorobenzylamine |
| 7 | 3-fluorobenzylamine |
| 8 | 2,5-difluorobenzylamine |
| 9 | 3,4-difluorobenzylamine |
| 10 | 2,6-difluorobenzylamine |
| 11 | 3-fluoro-5-(trifluoromethyl)-benzylamine |
| 12 | 4-(trifluoromethyl)-benzylamine |
| 13 | 4-(trifluoromethoxy)-benzylamine |
| 14 | 4-methoxybenzylamine |
| 15 | 2-methoxybenzylamine |
| 16 | 3,5-dimethoxybenzylamine |
| 17 | 3,4-dimethoxybenzylamine |
| 18 | 2,3-dimethoxybenzylamine |
| 19 | 2,4-dimethoxybenzylamine |
| 20 | 4-(aminomethyl)-benzenesulfonamide |
| 21 | 4-(dimethylamino)-benzylamine |
| 22 | aniline |
| 23 | 4-bromoaniline |
| 24 | diethylamine |
| 25 | tert. butylamine |
| 26 | dicyclohexylamine |
| 27 | propargylamine |
| 28 | allylamine |
| 29 | furfurylamine |
| 30 | cyclopropylmethylamine |
| 31 | N-benzylglycine ethyl ester |
| 32 | 2-fluorobenzylamine |
| 33 | 2-bromobenzylamine |
| 34 | 2-aminobenzylamine |
| 35 | 2-(4-methoxybenzylamino)-pyridine |
| 36 | N-benzyl-N',N'-dimethylethylene diamine |
| 37 | 3-(benzylamino)-propionitrile |
| 38 | 2-benzylamino pyridine |
| 39 | phenethylamine |
| 40 | 3-phenyl propylamine |
| 41 | 4-phenyl butylamine |
| 42 | (R)-1-phenylethylamine |
| 43 | (S)-1-phenylethylamine |
| 44 | 3-dimethylamino propylamine |
| 45 | (R)-2-amino-2-phenylethanol |
| 46 | (S)-2-amino-2-phenylethanol |
| 47 | N-benzyl ethanolamine |
| 48 | 2-amino methyl pyridine |
| 49 | 3-amino methyl pyridine |
| 50 | 4-amino methyl pyridine |
| 51 | penta fluorobenzylamine |

TABLE 2

| Example | Amide |
| --- | --- |
| 2 | (Z)-5-fluoro-2-methyl-1-(3,4,5-trimethoxybenzylidene)-3-(N-3-iodobenzyl)-indenylacetamide |
| 3 | (Z)-5-fluoro-2-methyl-1-(3,4,5-trimethoxybenzylidene)-3-(N-3-chlorobenzyl)-indenylacetamide |
| 4 | (Z)-5-fluoro-2-methyl-1-(3,4,5-trimethoxybenzylidene)-3-(N-2-chlorobenzyl)-indenylacetamide |
| 5 | (Z)-5-fluoro-2-methyl-1-(3,4,5-trimethoxybenzylidene)-3-(N-3,4-dichlorobenzyl)-indenylacetamide |
| 6 | (Z)-5-fluoro-2-methyl-1-(3,4,5-trimethoxybenzylidene)-3-(N-2,4-difluorobenzyl)-indenylacetamide |
| 7 | (Z)-5-fluoro-2-methyl-1-(3,4,5-trimethoxybenzylidene)-3-(N-3 -fluorobenzyl)-indenylacetamide |
| 8 | (Z)-5-fluoro-2-methyl-1-(3,4,5-trimethoxybenzylidene)-3(N-2,5-difluorobenzyl)-indenylacetamide |
| 9 | (Z)-5-fluoro-2-methyl-1-(3,4,5-trimethoxybenzylidene)-3-(N-3,4-difluorobenzyl)-indenylacetamide |
| 10 | (Z)-5-fluoro-2-methyl-1-(3,4,5-trimethoxybenzylidene)-3-(N-2,6-difluorobenzyl)-indenylacetamide |
| 11 | (Z)-5-fluoro-2-methyl-1-(3,4,5-trimethoxybenzylidene)-3-(N-3-fluoro-5-(trifluoromethyl)-benzyl)-indenylacetamide |
| 12 | (Z)-5-fluoro-2-methyl-1-(3,4,5-trimethoxybenzylidene)-3-(N-4-(trifluoromethyl)-benzyl)-indenylacetamide |
| 13 | (Z)-5-fluoro-2-methyl-1-(3,4,5-trimethoxybenzylidene)-3-(N-4-(trifluoromethoxy)-benzyl)-indenylacetamide |
| 14 | (Z)-5-fluoro-2-methyl-1-(3,4,5-trimethoxybenzylidene)-3-(N-4-methoxybenzyl)-indenylacetamide |
| 15 | (Z)-5-fluoro-2-methyl-1-(3,4,5-trimethoxybenzylidene)-3-(N-2-methoxybenzyl)-indenylacetamide |
| 16 | (Z)-5-fluoro-2-methyl-1-(3,4,5-trimethoxybenzylidene)-3-(N-3,5-dimethoxybenzyl)-indenylacetamide |
| 17 | (Z)-5-fluoro-2-methyl-1-(3,4,5-trimethoxybenzylidene)-3-(N-3,4-dimethoxybenzyl)-indenylacetamide |
| 18 | (Z)-5-fluoro-2-methyl-1-(3,4,5-trimethoxybenzylidene)-3-(N-2,3-dimethoxybenzyl)-indenylacetamide |
| 19 | (Z)-5-fluoro-2-methyl-1-(3,4,5-trimethoxybenzylidene)-3-(N-2,4-dimethoxybenzyl)-indenylacetamide |
| 20 | (Z)-5-fluoro-2-methyl-1-(3,4,5-trimethoxybenzylidene)-3-(N-4-sulfonamidobenzyl)-indenylacetamide |
| 21 | (Z)-5-fluoro-2-methyl-1-(3,4,5-trimethoxybenzylidene)-3-(N-4-(dimethylamino)-benzyl)-indenylacetamide |
| 22 | (Z)-5-fluoro-2-methyl-1-(3,4,5-trimethoxybenzylidene)-3-(N-phenyl)-indenylacetamide |
| 23 | (Z)-5-fluoro-2-methyl-1-(3,4,5-trimethoxybenzylidene)-3-(N-4-bromophenyl)-indenylacetamide |
| 24 | (Z)-5-fluoro-2-methyl-1-(3,4,5-trimethoxybenzylidene)-3-(N,N-diethyl)-indenylacetamide |
| 25 | (Z)-5-fluoro-2-methyl-1-(3,4,5-trimethoxybenzylidene)-3-(N-tertbutyl)-indenylacetamide |
| 26 | (Z)-5-fluoro-2-methyl-1-(3,4,5-trimethoxybenzylidene)-3-(N,N-dicyclohexyl)-indenylacetamide |
| 27 | (Z)-5-fluoro-2-methyl-1-(3,4,5-trimethoxybenzylidene)-3-(N-propargyl)-indenylacetamide (M.P. 171–172° C.) |
| 28 | (Z)-5-fluoro-2-methyl-1-(3,4,5-trimethoxybenzylidene)-3-(N-allyl)-indenylacetamide (M.P. 147–149° C.) |
| 29 | (Z)-5-fluoro-2-methyl-1-(3,4,5-trimethoxybenzylidene)-3-(N-furfuryl)-indenylacetamide (M.P. 166–167° C.) |
| 30 | (Z)-5-fluoro-2-methyl-1-(3,4,5-trimethoxybenzylidene)-3-(N-cyclopropylmethyl)-indenylacetamide (M.P. 150–151° C.) |
| 31 | (Z)-5-fluoro-2-methyl-1-(3,4,5-trimethoxybenzylidene)-3-(N-benzyl-N-glycinylethyl ester)-indenylacetamide |
| 32 | (Z)-5-fluoro-2-methyl-1-(3,4,5-trimethoxybenzylidene)-3-(N-2-fluorobenzyl)-indenylacetamide |
| 33 | (Z)-5-fluoro-2-methyl-1-(3,4,5-trimethoxybenzylidene)-3-(N-2-bromobenzyl)-indenylacetamide |
| 34 | (Z)-5-fluoro-2-methyl-1-(3,4,5-trimethoxybenzylidene)-3-(N-2-aminobenzyl)-indenylacetamide |
| 35 | (Z)-5-fluoro-2-methyl-1-(3,4,5-trimethoxybenzylidene)-3-(N-4-methoxybenzyl-N-(2-pyridinyl))-indenylacetamide |
| 36 | (Z)-5-fluoro-2-methyl-1-(3,4,5-trimethoxybenzylidene)-3-(N-benzyl-N-2-dimethylaminoethyl)-indenylacetamide |
| 37 | (Z)-5-fluoro-2-methyl-1-(3,4,5-trimethoxybenzylidene)-3-(N-benzyl-N-(2-cyanoethyl))-indenylacetamide |
| 38 | (Z)-5-fluoro-2-methyl-1-(3,4,5-trimethoxybenzylidene)-3-(N-benzyl-N-(2-pyridinyl))-indenylacetamide |
| 39 | (Z)-5-fluoro-2-methyl-1-(3,4,5-trimethoxybenzylidene)-3-(N-2- |

TABLE 2-continued

| Example | Amide |
|---|---|
| | phenylethyl)-indenylacetamide |
| 40 | (Z)-5-fluoro-2-methyl-1-(3,4,5-trimethoxybenzylidene)-3-(N-3-phenylpropyl)-indenylacetamide |
| 41 | (Z)-5-fluoro-2-methyl-1-(3,4,5-trimethoxybenzylidene)-3-(N-4-phenylbutyl)-indenylacetamide |
| 42 | (Z)-5-fluoro-2-methyl-1-(3,4,5-trimethoxybenzylidene)-3-(N-(R)-1-phenylethyl)-indenylacetamide |
| 43 | (Z)-5-fluoro-2-methyl-1-(3,4,5-trimethoxybenzylidene)-3-(N-(S)-1-phenylethyl)-indenylacetamide |
| 44 | (Z)-5-fluoro-2-methyl-1-(3,4,5-trimethoxybenzylidene)-3-(N-3-dimethylaminopropyl)-idenylacetamide |
| 45 | (Z)-5-fluoro-2-methyl-1-(3,4,5-trimethoxybenzylidene)-3-(N-(R)-1-hydroxy-2-phenylethyl)-idenylacetamide |
| 46 | (Z)-5-fluoro-2-methyl-1-(3,4,5-trimethoxybenzylidene)-3-(N-(S)-1-hydroxy-2-phenylethyl)-idenylacetamide |
| 47 | (Z)-5-fluoro-2-methyl-1-(3,4,5-trimethoxybenzylidene)-3-(N-benzyl-N-(1-hydroxyethyl))-idenylacetamide |
| 48 | (Z)-5-fluoro-2-methyl-1-(3,4,5-trimethoxybenzylidene)-3-(N-2-pyridinyl)-idenylacetamide |
| 49 | (Z)-5-fluoro-2-methyl-1-(3,4,5-trimethoxybenzylidene)-3-(N-3-pyridinyl)-idenylacetamide |
| 50 | (Z)-5-fluoro-2-methyl-1-(3,4,5-trimethoxybenzylidene)-3-(N-4-pyridinyl)-idenylacetamide |
| 51 | (Z)-5-fluoro-2-methyl-1-(3,4,5-trimethoxybenzylidene)-3-(N -pentafluorobenzyl)-idenylacetamide (MP 209–210° C.) |

EXAMPLE 52

(E)-5-Fluoro-2-methyl-1-(3,4,5-trimethoxybenzylidene)-3-(N-benzyl)-indenylacetamide When the residue from the evaporated mother liquor of preparation 1(E) is recrystallized from $CH_3CN$, there is obtained (E)-5-fluoro-2-methyl-1-(3,4,5-trimethoxybenzylidene)-3-indenylacetic acid, which is allowed to react with benzylamine according to the procedures of example 1 to give (E)-5-fluoro-2-methyl-1-(3,4,5-trimethoxybenzylidene)-3-(N-benzyl)-idenylacetamide, M.P. 149–152° C.

EXAMPLES 53–63

According to the procedures in Example 1, substituted benzaldehydes may be used in place of 3,4,5-trimethoxybenzaldehyde in step (E) at the same reaction conditions to obtain the corresponding acids. These acids may be used in place of (Z)-5-fluoro-2-methyl-1-(3,4,5-trimethoxybenzylidene)-3-indenylacetic acid in Example 1, steps (F) and (G), to obtain the corresponding benzylamides as listed in the examples below.

53) 2,4-dimethoxybenzaldehyde
(Z)-5-fluoro-2-methyl-1-(2,4-dimethoxybenzylidene)-3-(N-benzyl)-indenylacetamide (R and $R_1$=H, $R_2$=F, $R_3$ and $R_4$=H, $R_5$ and $R_6$=OCH$_3$, $R_7$=H, $R_8$=CH$_3$, o=1, M=PhCH$_2$NH)

54) 3,5-dimethoxybenzaldehyde
(Z)-5-fluoro-2-methyl-1-(3,5-dimethoxybenzylidene)-3-(N-benzyl)-indenylacetamide (R and $R_1$=H, $R_2$=F, $R_3$ and $R_4$=H, $R_5$=H, $R_6$ and $R_7$=OCH$_3$, $R_8$=CH$_3$, o=1, M=PhCH$_2$NH)

55) 2,4,6-trimethoxybenzaldehyde
(Z)-5-fluoro-2-methyl-1-(2,4,6-trimethoxybenzylidene)-3-(N-benzyl )-indenylacetamide (R and $R_1$=H, $R_2$=F, $R_3$ and $R_4$=H, $R_5$, $R_6$ an $R_7$=OCH$_3$, $R_8$=CH$_3$, o=1, M=PhCH$_2$NH) M.P. 224–225° C.

56) 4-chloro-3,5-dimethoxybenzaldehyde
(Z)-5-fluoro-2-methyl-1-(4-chloro-3,5-dimethoxybenzylidene)-3-(N-benzyl)-indenylacetamide (R and $R_1$=H, $R_2$=F, $R_3$and $R_4$=H, $R_5$=OCH$_3$, $R_6$=Cl, $R_7$=OCH$_3$, $R_8$=CH$_3$, o=1, M=PhCH$_2$NH)

57) 2,3,4-trimethoxybenzaldehyde
(Z)-5-fluoro-2-methyl-1-(2,3,4-trimethoxybenzylidene)-3-(N-benzyl)-indenylacetamide (R and $R_1$=H, $R_2$=F, $R_3$ and $R_4$=H, $R_5$, $R_6$ and $R_7$=OCH$_3$, $R_8$=CH$_3$, o=1, M=PhCH$_2$NH) M.P. 147–148° C.

58) 2,4,5-trimethoxybenzaldehyde
(Z)-5-fluoro-2-methyl-1-(2,4,5-trimethoxybenzylidene)-3-(N-benzyl)-indenylacetamide (R and $R_1$=H, $R_2$=F, $R_3$ and $R_4$=H, $R_5$, $R_6$ and $R_7$=OCH$_3$, $R_8$=CH$_3$, o=1, M=PhCH$_2$NH) M.P. 203–204° C.

59) 4-methyl-2,3-dimethoxybenzaldehyde
(Z)-5-fluoro-2-methyl-1-(4-methyl-2,3-dimethoxy-benzylidene)-3-(N-benzyl)-indenylacetamide (R and $R_1$=H, $R_2$=F, $R_3$ and $R_4$=H, $R_5$ and $R_6$=OCH$_3$, $R_7$=CH$_3$, $R_8$=CH$_3$, o=1, M=PhCH$_2$NH)

EXAMPLE 60

5-Methoxy-2-Methyl-1-(2,3.4-Trimethoxybenzylidene)-3-(N-benzal)-indenylacetamide (A) α-Methyl-β-(p-methylthiophenyl) propionic acid To a solution of 2.3 g (0.1 mol) of sodium in 100 ml of absolute alcohol is added 17.4 g (0.1 mol) of diethyl methylmalonate and 17.3 g (0.1 mol) of p-methylthiobenzylchloride. The mixture is heated under a reflux in a water bath for three hours. The reaction mixture is poured into water, and the aqueous solution is extracted six times with ether and dried. It is then evaporated to yield diethyl methyl-p-methylthiobenzyl malonate. The crude product is then saponified by heating with excess 4% sodium hydroxide in aqueous ethanolic solution. The solution thus formed is concentrated, extracted with ether to remove any neutral material, and acidified with dilute sulfuric acid. The acidic mixture is heated on a steam bath for one hour, cooled and then extracted with ether. Evaporation of the ether solution gives α-methyl-β-(p-methylthiophenyl) propionic acid.

With other substituted malonic esters in place of diethyl methylmalonate and other substituted benzyl halides in place of p-methylthiobenzoyl chloride, the corresponding substituted propionic acids are obtained, in a similar manner, for example:

α-methyl-β-(p-methoxyphenyl)propionic acid,

α-allyl-β-(p-nitrophenyl)propionic acid.

(B) 6-methoxy-2-methylindanone

α-Methyl-β-(p-methoxyphenyl)propionic acid (15 g) is added to polyphosphoric acid (170 g) at 50° C. and the mixture is heated at 83–90° C. for two hours. The syrup is poured into iced water, stirred for one-half hour, and then extracted with ether three times. The ether solution is washed with water twice, and with 5% NaHCO$_3$ five times until all the acidic material has been removed. The remaining neutral solution is washed with water and dried over sodium sulfate. Evaporation of the solution gives the indanone as a pale yellow oil.

Other β-aryl propionic acid compounds are converted to the corresponding indanone by the procedure of this example in a similar manner.

(C) Methyl 5-methoxy-2-methyl-3-indenylacetate.

A solution of 13.4 g of 6-methoxy-2-methylindanone and 19.3 g of methyl bromoacetate in 45 ml benzene is added over a period of 5 minutes to 21 g of zinc amalgam (prepared according to *Organic Synthesis,* Coll. Vol. 3, p. 444) in 110 ml benzene and 40 ml dry ether. A few crystals of iodine are added to start the reaction, and the reaction mixture is maintained at reflux temperature (ca. 65° C.). At 3 hour intervals, two batches of 10 g zinc amalgam and 10 g methyl bromo acetate are added. The mixture is then refluxed for 8 hours. After addition of 30 ml ethanol and 150 ml of acetic acid, the mixture is poured into 700 ml of 50% aqueous acetic acid. The organic layer is separated, and the aqueous layer is extracted twice with ether. The combined organic layers are washed thoroughly with water, ammonium hydroxide and water.

Drying over sodium sulfate, evaporation of solvent in vacuo, followed by pumping at 80° C. (bath temp.) (1–2 mm.) gives crude methyl(1-hydroxy-2-methyl-methoxy-indenyl)acetate.

A mixture of the above crude hydroxyester, 20 g of p-toluenesulfonic acid monohydrate and 20 g of anhydrous calcium chloride in 250 ml toluene is refluxed overnight. The solution is filtered, and the solid residue is washed with benzene. The combined benzene solution is washed with water, sodium bicarbonate, and water, and is then dried over sodium sulfate. After evaporation, the residual crude methyl 5-methoxy-2-methyl-3-indenylacetate is chromatographed on acid-washed alumina, and the product is eluted with petroleum ether-ether (v./v. 50–100%).

METHYL 2,6-DIMETHYL-3-INDENYLACETATE

The above reactions of Example 60(C) are repeated except that the starting materials are 2,5-dimethylindanone and methylbromoacetate. Using the same reaction conditions and techniques there is obtained methyl 2,6-dimethyl-3-indenylacetate.

The above reaction s of Example 60(C) are repeated except that the starting materials are 6-methylthioindanone and methylbromoacetate. Using the same reaction conditions and techniques, there is obtained methyl 5-methyl-thio-2-methyl-3-indenyl-acetate.

When any of the other indanones described in the other examples of the specification are used in the above procedure in place of 6-methoxy-2-methylindanone the corresponding methyl ester is obtained.

(D) 5-methoxy-2-methyl-1-(2,3,4-trimethoxybenzylidene)-3-indenyl acetic acid.

To a solution of methyl 5-methoxy-2-methyl-3-indenylacetate 8.7 g (0.037 mol) and 2,3,4-trimethoxybenzaldehyde, 7.99 g (1.1 equivalent) is added 16+ ml (2.0+ equivalents) of 25% methanolic sodium methoxide. The mixture is stirred at reflux under nitrogen for 2 hours. An equal volume of water is added dropwise and refluxing continues for 30 min. The solution is cooled, diluted with water and extracted with ether (3×). Residual ether is blown off with nitrogen, and then the aqueous solution is acidified with 50% glacial acetic acid. The precipitated product is collected and washed thoroughly with water. The crude product is crystallized to give 5-methoxy-2-methyl-1-(2,3,4-trimethoxybenzylidene)-3-indenyl acetic acid.

(E) 5-methoxy-2-methyl-1-(2,3,4-trimethoxybenzylidene)-3-(N-benzyl)-indenylacetamide Following the procedures of Example 1(F) and (G) and using the acid described above leads to the formation of the title compound. (R and $R_1$=H, $R_2$=OCH$_3$, $R_3$ and $R_4$=H, $R_5$, $R_6$ and $R_7$=OCH$_3$, $R_8$=CH$_3$, o=1, M=PhCH$_2$NH)

EXAMPLE 61

5-Methoxy-2-Methyl-1-(3,4,5-Trimethoxy-Benzylidene)-3-(N-Benzyl)-Indenylacetamide The above reaction of Example 60(D) and (E) is repeated with 3,4,5-trimethoxybenzaldehyde instead of 2,3,4-trimethoxy-benzaldehyde. With the same reaction conditions and techniques, 5-methoxy-2-methyl-1-(3,4,5-trimethoxybenzylidene)-3-(N-benzyl)-indenylacetamide is obtained. (R and $R_1$=H, $R_2$=OCH$_3$, $R_3$ and $R_4$=H, $R_5$, $R_6$ and $R_7$=OCH$_3$, $R_8$=CH$_3$, o=1, M=PhCH$_2$NH)

EXAMPLE 62

5-Hydroxy-2-Methyl-1-(2,4,6-Trimethoxy-Benzylidene)-3-(N-Benzyl)-Indenylacetamide The reactions of Example 60(D) and (E) are repeated with methyl 5-hydroxy-2-methyl-3-indenylacetate and 2,4,6-trimethoxybenzaldehyde as starting, materials, and 5-hydroxy-2-methyl-1-(2,4,6-trimethoxybenzylidene)-3-(N-benzyl)-indenylacetamide is obtained. (R and $R_1$=H, $R_2$==OH, $R_3$ and $R_4$=H, $R_5$, $R_6$ and $R_7$=OCH$_3$, $R_8$=CH$_3$, o=1, M=PhCH$_2$NH)

The other methyl esters of Example 60(C) react with 2,4,6-trimethoxybenzaldehyde according to the above procedure to produce the corresponding (N-benzyl) indenyl acetamide.

EXAMPLE 63

5-Methoxy-2-Methyl-1-(2,4,5-Trimethoxybenzylidene)-3-(N-Benzyl)-Indenyl Acetamide (A) 6-methoxy-2-methylindanone.

In a 500 ml 3-necked flask is placed 36.2 g (0.55 mol) of zinc dust, and a 250 ml addition funnel is charged with a mixture of 80 ml anhydrous benzene, 20 ml of anhydrous ether, 80 g (0.58 mol) of p-anisaldehyde and 98 g (0.55 mol) of ethyl-2 -bromopropionate. About 10 ml of the mixture is added to the zinc dust with vigorous stirring, and the suspension is warmed gently until an exothermic reaction commences. The remaining reactants are added dropwise at such a rate that the reaction mixture is refluxing smoothly on its own accord (ca. 30–35 min.). After addition is completed, the flask is placed in a water bath, the suspension is heated at reflux for 30 minutes, and is cooled to 0° C. Sulfuric acid (250 ml, 10%) is added with vigorous stirring. The benzene layer is extracted twice with 50 ml portions of 5% sulfuric acid and washed with 50 ml portions of sulfuric acid (2×) and 50 ml portions of water (2×). The aqueous acidic layers are combined and extracted with 2×50 ml ether. The combined ether and benzene extracts are dried over sodium sulfate. Evaporation of solvent and fractionation of the residue through a 6" Vigreux column affords the product, ethyl-2-hydroxy-(p-methoxyphenyl)-1-methylpropionate, B.P. 155–160° C. (1.5 mm).

By the method described in Vanden Zanden, Rec. trav. chim., 68, 413 (1949), the above compound is converted to 6-methoxy-2-methylindanone.

5-ETHYL-2-METHYLINDANONE

The above reactions of Example 63(A) are repeated except that the starting materials are o-ethylbenzaldehyde and ethyl-2-bromopropionate. By using the same reaction conditions and techniques, there is obtained 5-ethyl-2-methylindanone.

When the benzaldehydes listed in Table 3 below are used in the procedure of Example 63A, the corresponding indanone is obtained.

TABLE 3

| Aldehyde | Indanone |
| --- | --- |
| p,-o-, or m-tolualdehyde | 2,6-dimethyl, 2,5-dimethyl, or 2,4-dimethyl-indanone |
| p,-o-, or m-hydroxybenzaldehyde | 4, 5 or 6-hydroxy-2-methylindanone |
| p,-o-, or nitrobenzaldhyde | 2-methyl-(4, 5 or 6) nitroindanone |
| p,-o-, or m-chlorobenzaldehyde | (4, 5, or 6)-chloro-2-methylindanone |
| p,-o-, or m-cyanobenzaldehyde | (4, 5, or 6)-cyano-2-methylindanone |
| vanillin | 6-hydroxy-5-methoxy-2-methylindanone |
| p,-o-, or m-sulfamylbenzaldehyde | 2-methyl-(4,5 or 6)-sulfamylindanone |
| 3-chloro-4-methylbenzaldehyde | 5-chloro-2,6 dimethylindanone |
| 4-carbamide-5-methylbenaldehyde | 6-carbomide-2,5 dimethylindanone |
| 3,4-difluorobenzaldehyde | 5,6-difluoro-2-methylindanone |
| 3,4,5-trifluorobenzaldehyde | 5,6,7-trifluoro-2-methylindanone |

(B) 5-methoxy-2-methyl-1-(2,4,5-trimethoxybenzylidene)-3-(N-benzyl)-indenyl acetamide The reactions of Examples 60(C)–(E) are repeated, and 5-methoxy-2-methyl-1-(2,4,5-trimethoxybenzylidene)-3-(N-benzyl)-indenylacetamide is obtained.

EXAMPLE 64

1-(3,4,5-Trimethoxybenzylidene)-2-Methyl-5-Methoxy-3-Indenyl-(N-Benzyl)-Propionamide (A) Methyl-α(5-methoxy-2-methyl-3-indenyl) propionate.

The procedure of Example 60(C) is followed using methyl α-bromopropionate in equivalent quantities in place of methyl bromoacetate used therein. There is obtained methyl α-(1-hydroxy-6-methoxy-2-methyl-1-indenyl) propionate, and it is then dehydrated to methyl α-(5-methoxy-2-methyl-3-indenyl)propionate in the same manner.

(B) α-[1-(3,4,5-trimethoxybenzylidene)-2-methyl-5-methoxy-3-indenyl] propionic acid To a solution of 0.5 g (1.92 mmol) of methyl α-(5-methoxy-2-methyl-3-indenyl) propionate and 0.77 g (3.9 mmol) of 3,4,5-trimethoxybenzaldehyde in 3 ml of anhydrous pyridine is added 1.63 g of a 40% solution of benzyltrimethylammonium hydroxide (Triton-B) in methanol. The resulting red-purple solution is stirred at room temperature overnight.

The reaction mixture is poured into a mixture of ice and water, acidified with 2.5 N HCl, and extracted with ether. The ether solution is then washed with 2.5 N HCl until the washing acidifies (once), then with water until neutral. The ether layer is then extracted with 5% $Na_2CO_3$ solution. The $Na_2CO_3$ solution is washed with ether, acidified and extracted with ether. The ether solution is washed with water, dried over $Na_2SO_4$ and concentrated in vacuo to obtain α-[1-(3,4,5-trimethoxybenzylidene)-2-methyl-5-methoxy-3-indenyl] propionic acid.

(C) 1-(3,4,5-Trimethoxybenzylidene)-2-methyl-5-methoxy-3-indenyl -(N-benzyl)-propionamide Following the procedure of Example 1(G) and using the acid described above leads to the formation of the title compound. ($R=CH_3$, $R_1=H$, $R_2=OCH_3$, $R_3$ and $R_4=H$, $R_5$, $R_6$ and $R_7=OCH_3$, $R_8=CH_3$, o=1, $M=PhCH_2NH$)

EXAMPLE 65

1-(2,4,6-Trimethoxybenzylidene)-5-Dimethylamino-2-Methyl-3-(N-Benzyl)-Indenyl Acetamide (A) Methyl-3-hydroxy-2-methyl-5-nitro-3-indenylacetate The procedure of Example 60(C) is followed using 2-methyl-6-nitro indanone in equivalent quantities in place of 6-methyoxy-2-methyl-indanone used therein. After the mixture is condensed, 30 ml of ethanol and 50 ml of acetic acid are added. The mixture is then poured into 700 ml of water. Extraction with ether gives methyl 3-hydroxy-2-methyl-5-nitro-3-indenylacetate.

(B) Methyl 5-dimethylamino-2-methyl-3-indenylacetate.

A solution of 0.05 mol of methyl 3-hydroxy-2-methyl-5-nitro-3-indenylacetate, 0.2 mol of 38% aqueous formaldehyde and 2 ml of acetic acid in 100 ml ethanol is reduced catalytically in the presence of a 10% Pd/C catalyst under 40 lb p.s.i. hydrogen pressure at room temperature. The solution is filtered, evaporated and chromatographed on 300 g of silica gel to give methyl 5-dimethylamino-3-hydroxy-2-methyl-3-indenylacetate. The hydroxy ester is then dehydrated to methyl 5-dimethylamino-2-methyl-3-indenylacetate.

(C) 1-(2,4,6-trimethoxybenzylidene)-5-dimethylamino-2-methyl -3-indenyl acetic acid.

To a solution of 2.5 g of the ester from Part B of this example in 15 ml of 1,2-dimethoxyethane at 0° C. is added 1.95 g of 2,4,6-trimethoxybenzaldehyde followed by 1.1 g of potassium t-butoxide. The reaction mixture is kept in the ice-bath for 4 hours, and then allowed to stand at room temperature for 18 hours. The mixture is diluted with 15 ml of ether and the potassium salt is filtered. The salt is dissolved in 30 ml of water and neutralized with dilute hydrochloric acid to pH 6–6.5. The crude acid precipitated is collected by filtration and re-crystallized to give 1-(2,4,6-trimethoxybenzylidene)-5-dimethylamino-2-methyl-3-indenyl acetic acid.

(D) 1-(2,4,6-Trimethoxybenzylidene)-5-dimethylamino-2-methyl-3-(N-benzyl)-indenylacetamide Following the procedure of Example 1(G) and using the acid described above leads to the formation of the title compound. (R and $R_1$=H, $R_2$=N($CH_3$)$_2$, $R_3$ and $R_4$=H, $R_5$, $R_6$ and $R_7$=OCH_3, $R_8$=CH_3, o=1, $M=PhCH_2NH$)

EXAMPLE 66

α-[1-(3,4,5-Trimethoxybenzylidene)-2-Methyl-5-Dimethylamino-3-Indenyl]-(N-Benzyl)-Propionamide (A) α-[1-(3,4,5-trimethoxybenzylidene)-2-methyl-5-dimethylamino-3-indenyl]-propionic acid.

The procedures of Examples 63(A) and (B) are followed using 6-dimethylamino-2-methylindanone in place of 6-methoxy-2-methylindanone and methyl-α-bromopropionate in place of methyl bromoacetate used therein. There is obtained α-[1-(3,4,5-trimethoxybenzylidene)-2-methyl-5-dimethylamino-3-indenyl]-(N-benzyl)-propionamide. ($R=CH_3$, $R_1=H$, $R_2$=N($CH_3$)$_2$, $R_3$ and $R_4$=H, $R_5$, $R_6$ and $R_7$=OCH_3, $R_8$=CH_3, o=1, $M=PhCH_2NH$)

EXAMPLE 67

5,6-Difluoro-2-Methyl-1-(3,4,5-Trimethoxybenzylidene)-3-(N-Benzyl)-Indenyl Acetamide (A) 3,4-difluorobenzaldehyde, In a 250 ml three-necked flask equipped with a magnetic stirrer, thermometer, condenser, and dropping funnel is placed 25.6 g (0.2 mol) of 3,4 difluorotoluene. The liquid is heated to 105° C. and illuminated as 67 g (0.42 mol) of bromine is added slowly. The temperature is kept between 105–110° C. while the first half of the bromine is added over a period of one hour. The rest of the bromine is added over approximately a 2-hour period and the temperature is raised to 150° C. and kept there for 5 minutes.

The reaction mixture is cooled and transferred to a 1 liter 3-necked flask with a motor driven stirrer and condenser. 120 ml $H_2O$ and 90 g of calcium carbonate are added, and the mixture is refluxed for 20 hours with good stirring. The reaction mixture is steam distilled until no further oil is collected. The oil is taken up in methylene chloride and dried over $MgSO_4$. Evaporation of the solvent yields 3,4-difluorobenzaldehyde which is used without further purification.

(B) 3,4-difluoro-α-methylcinnamic acid.

A mixture of 2.88 g (0.02 mol) of 3,4-difluorobenzaldehyde, 3.24 g (0.025 mol) of propionic anhydride and 0.92 g (0.02 mol) of sodium propionate under nitrogen is heated at 135° C. with a magnetic stirrer for 20 hours. The reaction mixture is poured onto 50 ml of water. A solid precipitates that dissolves when 50 ml of saturated $K_2CO_3$ is added with stirring. The basic solution is extracted with ether (2×100 ml). The aqueous phase is then poured into an excess of concentrated HCl and ice. The precipitated white solid is filtered and dried to give 3,4-difluoro-ox-methylcinnamic acid, M.P. 122–125° C.

4-TRIFLUOROMETHYL-α-METHYLCINNAMIC ACID

The above reaction of Example 67(B) is repeated except that 4-trifluoromethylbenzaldehyde is used as a starting material in place of 3,4-difluorobenzaldehyde. Using the same reaction conditions and techniques there is obtained 4-trifluoromethyl-α-methylcinnamic acid.

By similarly using other benzaldehydes such as 4-methylthiobenzaldehyde, 4-chlorobenzaldehyde, and 3-methyl-4-chlorobenzaldehyde, there is obtained 4-methylthio-α-methylcinnamic acid, 4-chloro-α-methylcinnamic acid and 3-methyl-4-chloro-α-methylcinnamic acid respectively.

(C) 3,4-difluoro-α-methylhydrocinnamic acid.

A mixture of 28 g (0.141 mol) of 3,4-difluoro-ot-methylcinnamic acid, 1 g of $PtO_2$, and 250 ml of MeOH is hydrogenated at 45 p.s.i. until the theoretical uptake is completed. The catalyst is filtered off, and the material evaporated to one-third its volume. A 15% potassium hydroxide solution (10 ml) is added, and the mixture refluxed for 30 minutes, is poured into water, and is extracted with ether (2×100 ml). The aqueous layer is acidified with concentrated HCl and ice. The oil which separates is extracted into ether, the ether solution dried over $MgSO_4$ and evaporated to leave a clear oil which crystallizes. 3,4-difluoro-α-methylhydrocinnamic acid, M.P. 55–56° C., is isolated.

(D) 5,6-difluoro-2-methyl-1-indanone.

20 g (0.1 mol) of 3,4-difluoro-α-methylhydrocinnamic acid is added to 250 g of polyphosphoric acid. The mixture is efficiently stirred and heated on a steam bath for 2 hours. The mixture is poured onto ice-water (400 ml). The precipitate is extracted with ether (3×100 ml). The extract is washed with saturated potassium carbonate, water and then dried ($MgSO_4$). The ether solution, when evaporated, leaves solid 5,6-difluoro-2-methyl-1-indanone (M.P. 66–68° C.) which is used without further purification.

(E) 5,6-difluoro-2-methylindene-3-acetic acid methyl ester.

A mixture of 9.1 g (0.05 mol) of 5,6-difluoro-2-methyl-1-indanone, 4.0 g of "activated" zinc dust, 7.6 g (0.05 mol) of methyl bromoacetate, and a crystal of iodine in 250 ml of dry benzene is refluxed for 4–5 hours. TLC (20% $Et_2O$-80% pet. ether on Si gel) shows greater than 95% conversion at this time. The reaction mixture is poured onto 250 ml of 5% $H_2SO_4$ The organic phase was dried ($MgSO_4$). Removal of solvent leaves an oily hydroxy ester, which is redissolved in 100 ml of benzene, and is refluxed with phosphorus pentoxide (20 g) for 30 minutes. The organic layer is decanted, the residue is washed with benzene, and the combined organic layers are washed with water (2×100 ml) and dried ($MgSO_4$). The benzene, when evaporated, leaves 5,6-difluoro-2-methylindene-.3-acetic acid methyl ester, M.P. 86–90° C.

5-METHYLTHIO-2-METHYLINDENE-3-ACETIC ACID METHYL ESTER

The above reaction of Example 67(E) is repeated using 5-methylthio-2-methylindanone instead of 5,6-difluoro-2-methyl-1-indanone. Using the same conditions and techniques, there is obtained 5-methylthio-2-methylindene-3-acetic acid methyl ester.

When an acylamino or sulfonyl indanone is employed as the starting material in the above procedure, the corresponding methyl ester is obtained.

(F) 5,6-difluoro-2-methyl-1-(3,4,5-trimethoxybenzylidene)-indenyl-3-acetic acid.

1.19 g (5.0 mmol) of 5,6-difluoro-2-methylindene-3-acetic acid methyl ester is dissolved in 10 ml of dry pyridine followed by 0.98 g (5.0 mmol) of 3,4,5-trimethoxybenzaldehyde. The flask is placed under nitrogen, and 5.0 g (5.1 mol) of Triton B is added. The deeply colored solution is allowed to stand overnight. Water (2 ml) is added. After standing for 15 minutes, the mixture is poured into an excess of water. The organics are extracted with ether (2×50 ml). The aqueous phase is added to 10% HCl-ice. The orange, gummy solid that precipitates is extracted into methylene chloride and dried ($MgSO_4$). The solvent is removed to leave an orange solid. The solid is filtered to give a crude product which is recrystallized to give 5,6-difluoro-2-methyl-1-(3,4,5-trimethoxy-benzylidene)-indene-3-acetic acid. When 2,4,6-trimethoxybenzaldehyde or 2,4,5-trimethoxybenzdehyde is used in the above procedure, instead of 3,4,5-trimethoxy-benzaldehyde, the corresponding indene acetic acid is obtained.

(G) 5,6-Difluoro-2-methyl-1-(3,4,5-trimethoxybenzylidene)-3-(N-benzyl)-indenylacetamide Following the procedure of Example 1(G) and using the acid described above leads to the formation of the title compound. (R and $R_1$=H, $R_2$ and $R_3$=F, $R_4$=H, $R_5$, $R_6$ and $R_7$=$OCH_3$, $R_8$=$CH_3$, o=1, M=$PhCH_2NH$)

EXAMPLE 68

5,6-Difluoro-2-Methyl-1-(3,4,5-Trimethoxnbenzylidene)-3-(N-Benzyl)-Indenylacetamide (A) 3,4-difluorobenzaldehyde.

57 g (0.5 mol) of ortho-difluorobenzene in 250 ml of methylene chloride is added to 100 g (0.75 mol) of anhydrous aluminum chloride. The mixture is stirred mechanically at 0° C. (ice bath) while 85.5 g (0.75 mol) of dichloromethyl methylether is added dropwise. Vigorous HCl evolution takes place, and the reaction mixture turns orange-red. After the addition, the mixture is stirred at room temperature for 15 minutes, and the liquid phase is decanted into 500 ml of ice and water. The residue in the reaction flask is washed with methylene chloride until colorless, and the washings are added to the water. The mixture is shaken well in a separatory funnel until the methylene chloride layer is green. The organic layer is washed with saturated potassium carbonate solution until neutral, is dried $MgSO_4$) and is distilled to give 3,4-difluorobenzaldehyde, B.P. 70–74° C./20 mm. The dark residue in the distillation pot solidifies on cooling to give tris-(3,4-difluorophenyl)methane, M.P. 95–96° C.

3,4-DIMETHYLBENZALDEHYDE

The above reaction of Example 68(A) is repeated except that o-xylene and dichloromethyl methylether are the starting materials. Using the same reaction conditions and techniques, there is obtained 3,4-dimethylbenzaldehyde.

4-MERCAPTOBENZALDEHYDE

The above reaction of Example 68(A) is repeated except that the starting materials are mercaptobenzene and dichloromethyl methylether. Using the same reaction conditions and techniques, there is obtained 4-mercaptobenzaldehyde.

(B) 5,6-difluoro-2-methyl-1-(3,4,5-trimethoxybenzylidene)-3-(N-Benzyl)-indenylacetamide The reactions of Examples 67(B)–(G) are repeated and 5,6-difluoro-2-methyl-1-(3,4,5-trimethoxy-benzylidene)-3-(N-Benzyl)-indenylacetamide is obtained. (R and $R_1$ and $R_3$=F, $R_4$=H, $R_5$, $R_6$ and $R_7$=$OCH_3$, $R_8$=$CH_3$, o=1, M=$PhCH_2NH$)

Similarly, when 3,4-dimethylbenzaldehyde is used in the reactions in Example 68(B), 5,6-dimethyl-2-methyl-1-(3,4,5-trimethoxy-benzylidene)-3-(N-benzyl)-indenylacetamide is obtained. ($R_2$ and $R_3$=$CH_3$).

When 4-mercaptobenzaldehyde is used in the reactions in Example 68(B), 6-mercapto-2-methyl-1-(3,4,5-trimethoxy-benzylidene)-3-(N-benzyl)-indenylacetamide is obtained. ($R_2$=H, $R_3$=SH, $R_4$=H)

EXAMPLE 69

α-1-(3,4,5-Trimethoxybenzylidene)-2-Methyl-5-Methoxy-6-Fluoro-3-(N-Benzyl)-Indenylacetamide (A) 3-fluoro-4-methoxybenzaldehyde.

A solution of o-fluoroanisole, 101 g (0.80 mol) in 500 ml dry methylene chloride is added dropwise over 30 minutes to a solution of titanium tetrachloride, 182 g (0.96 mol, 1.2 equiv.) and a,(x-dichloromethylmethyl ether, 110 g (0.96 mol) in an equal volume of methylene chloride. The temperature is maintained at 10–20° C. with an ice-bath. The mixture is stirred at room temperature for 1 hour longer and then poured over crushed ice-water with stirring. Ether (1) is added, and the mixture stirred under nitrogen until solution occurs. The organic layer is extracted with water (3×), with sodium bicarbonate solution (3×) and is dried ($MgSO_4$). The solvent is evaporated at 30° C. to give an oily crude product, which is distilled in vacuo through a jacketed Vigreux column to give 3-fluoro-4-methoxybenzaldehyde, B.P. 120–121° C. (10 mm Hg) $R_f$0.6 on a silica-gel G with methylene chloride.

(B) 3-fluoro-4-methoxy-α-methylcinnamic acid.

A mixture of 3-fluoro-4-methoxybenzaldehyde, 34.2 g (0.22 mol), propionic anhydride, 50 g (0.38 mol) and sodium propionate, 21 g (0.22 mol) is stirred under nitrogen at 1 50° C. for 15 hours. The reaction mixture is then poured into 1.3 1 of water with stirring, and the product is precipitated. 2.0 N potassium hydroxide solution (500 ml) is added, and the mixture is stirred for several hours, until the precipitate has dissolved.

The aqueous solution is extracted with ether (3×) and is acidified with concentrated hydrochloric acid with stirring. The precipitated product is collected, is washed thoroughly with water, and is dried in a vacuum oven at 50° C. over potassium hydroxide pellets to give 3-fluoro-u..methyl-4-methoxycinnamic acid, M.P. 167–169° C.; $R_f$0.5 on silica-gel G with methylene chloride-methanol (1:1).

(C) 3-fluoro-4-methoxy-α-methyl dihydrocinnamic acid.

3-Fluoro-4-methoxy-α-methylcinnamic acid (49.5 g 0.236 mol), in 800 ml methanol is hydrogenated at 43 lbs. pressure and room temperature until the theoretical uptake of hydrogen has occurred (24 min at 20° C., using 1.5 g platinum oxide catalyst).

The solution is filtered, and is evaporated with warming to 60° C. to give 3-fluoro-4-methoxy-α-methyl dihydrocinnamic acid ($R_f$0.5 on silica-gel G with methylene chloride-methanol, 9:1 )

(D) 5-fluoro-6-methoxy-2-methylindanone.

A mixture of 3-fluoro-α-methyl-4-methoxy dihydrocinnamic acid, 49.3 g (0.23 mol) in 500 g of polyphosphoric acid is heated at 95° C. on a steam bath with occasional agitation for 75 min. The dark red solution is poured into 3.0 liters of water, and the mixture is stirred overnight. The precipitated product is collected, is washed thoroughly with water and is dissolved in ether. The ether solution is extracted with aqueous potassium bicarbonate (4×), diluted with methylene chloride, and dried ($MgSO_4$).

The organic solution is evaporated and recrystallized from methylene chloride-petroleum ether to give 5-fluoro-6-methoxy-2-methylindanone (M.P. 76–78° C.).

(E) Methyl 6-fluoro-5-methoxy-2-methyl-3-indenylacetate.

Into a 500 ml three-necked flask fitted with mechanical stirrer, reflux condenser, drying tube, dropping funnel and nitrogen inlet is placed 8.0 g zinc sheet and 100 ml of dry benzene. A crystal of iodine is added. A solution of 21.3 g (0.11 mol) of 5-fluoro-6-methoxy-2-methylindanone and 18.36 g (0.121 mol) of methyl bromoacetate in 100 ml of dry benzene is added in increments of a few milliliters. The mixture is gently heated with stirring. After the iodine color has disappeared, and the remainder of the mixture is added gradually, the reaction flask is heated at reflux temperature for about 18 hours The mixture is poured onto 600 ml of 5% $H_3SO_4$ and about 500 g of ice. Some ether is added. The organic layer is separated and washed with three portions of 5% $H_2SO_4$ water, $KHCO_3$ solution and finally water again. The organic layer is dried ($MgSO_4$) and concentrated to give 27.6 g of reddish oil which crystallizes upon standing. Thin-layer chromatography on silica-gel G with methylene chloride methanol (99:1 ) shows product at $R_f$(0.5).

Without further purification, the hydroxy ester is dehydrated to the indenylacetate. In 200 ml of dry benzene, 14.2 g (53 mol) of crude ester and 36 g of phosphorus pentoxide are refluxed with stirring for ½ hour. After cooling, the reaction mixture is filtered and the solid residue washed well with benzene. The benzene filtrate is washed with two portions of salt water and dried ($MgSO_4$). The organic solution is concentrated and gives a slightly colored oil which rapidly crystallizes. The crude product is recrystallized from methylene chloride-petroleum ether to give methyl-6-fluoro-5-methoxy-2-methyl-3-indenylacetate (M.P. 61–62° C.).

(F) 6-fluoro-5-methoxy-2-methyl-1-(3,4,5-trimethoxybenzylidene)-3-indenyl acetic acid.

To a solution of methyl-6-fluoro-5-methoxy-2-methyl-3-indenyl acetate, 9.3 g (0.037 mol) and 3,4,5-trimethoxybenzaldehyde, 7.99 g (1.1 equivalent) is added 16 ml (2.0 equivalents) of 25% methanolic sodium methoxide. The mixture is stirred at reflux under nitrogen for 2 hours. An equal volume of water is added dropwise and refluxing continues for 30 minutes. The solution is cooled, diluted with water and extracted with ether (3x). Residual ether is blown off with nitrogen, and then the aqueous solution is acidified with 50% glacial acetic acid. The precipitated product is collected and washed thoroughly with water. The crude product is recrystallized to give 6-fluoro-5-methoxy-2-methyl-1-(3,4,5-trimethoxybenzylidene)-3-indenyl acetic acid.

(G) 6-fluoro-5-methoxy-2-methyl-1-(3,4,5-trimethoxybenzylidene)-3-(N-benzyl)-indenylacetamide Following the procedures of Example 1(F) and (G) and using the acid described above leads to the formation of the title compound. (R and $R_1$=H, $R_2$=$OCH_3$, $R_3$=F, $R_4$=H, $R_5$, $R_6$ and $R_7$=$OCH_3$, $R_8$=$CH_3$, o=1, M=$PhCH_2NH$)

EXAMPLE 70

Cis-5,7-Difluoro-2-Methyl-1-(3,4,5-Trimethoxybenzylidene)-3-(N-Benzyl)-Indenyl Acetamide (A) 2,4-difluorobenzaldehyde.

A 250 ml, three-necked flask is fitted with a stirrer, a thermometer, a dropping funnel with a long stem to the bottom of the flask and a reflux condenser with a tube leading to the back of a hood. 50 g (0.38 mol) of 2,4-difluorotoluene is heated to reflux with stirring and irradiated with a Hanovia ultraviolet lamp. 41.5 ml of bromine is gradually added. The reaction is completed in 2.5 hours during which time the reflux temperature rises from 112° C. to 155° C.

A 2 l three-necked flask is fitted with a stirrer and reflux condenser. In the flask is placed 200 ml of water and 140 g calcium carbonate. The cooled above-described reaction mixture is transferred into the 2l three-necked flask using some ether for rinsing. The hydrolysis is completed by refluxing the reaction mixture with stirring for 18 hours. The aldehyde is isolated by steam distillation. The oil is separated and the aqueous phase is extracted once with ether. The oil and ether extracts are combined and dried over anhydrous $MgSO_4$ and concentrated under reduced pressure. The obtained 2,4-difluorobenzaldehyde, contains some ether and is purified by distillation over a short Vigreux column under reduced pressure. B.P. 56–58° C. 12 mm.

(B) 2,4-difluoro-αx-methylcinnamic acid.

A 500 ml, three-necked flask is fitted with a reflux condenser, drying tube, stirrer and $N_2$ inlet. To a mixture of 55.4 g (0.39 mol) of 2,4-difluorobenzaldehyde and 56 ml of propionic anhydride is added 38 g (0.39 mol) of sodium propionate. The reaction mixture is heated at 135–140° C. (oil bath temp.) for 19 hours with stirring under nitrogen. The still warm solution is poured into 1 l of water with stirring. A solid separates, which is dissolved by 56 g of potassium hydroxide. The solution is extracted with ether. The water phase is heated on the steam bath to remove the ether. After cooling in an ice-bath, concentrated hydrochloric acid is added with stirring. The solid which separates is collected and washed with cold water. Drying at 60° C. over KOH gives 2,4-difluoro-α-methylcinnamic acid, M.P. 126–128° C.

(C) 2,4-difluoro-α-methyldihydrocinnamic acid.

In 800 ml of methanol, 60 g (0.3 mol) of 2,4-difluoro-α-methylcinnamic acid with 1.5 g of platinum oxide catalyst is shaken under an initial pressure of 42 lbs of hydrogen until one equivalent of hydrogen is absorbed. The reaction time is 30 minutes. The catalyst is removed by filtration and washed with methanol. The methanol is evaporated off. The residue, a near-colorless oil, 2,4-difluoro-α-methyldihydrocinnamic acid, is used in the next step without further purification.

(D) 4,6-difluoro-2-methylindanone.

A solution of 2,4-difluoro-α-methyldihydrocinnamic acid, 54.8 g (0.274 mol) in 125 ml thionyl chloride is stirred for 90 minutes, at room temperature, and then refluxed for 90 minutes. The thionyl chloride is evaporated under reduced pressure. The acid chloride is obtained as an oil.

To a suspension of powdered aluminum chloride, 60 g (0.45 mol), in 250 ml of dry carbon disulfide at 0° C. is added dropwise over a period of 10 minutes, a solution of the acid chloride, 60 g, in 100 ml carbon disulfide. After the addition, the ice bath is removed, and the temperature raised slowly to room temperature. The mixture is stirred at room temperature for 20 hours, and then is poured into 2 l of 10% aqueous hydrochloric acid-crushed ice with stirring. Ether is added, and the stirring is continued until everything dissolves. The ether layer is separated, is extracted with 5% hydrochloric acid (2x), water (2x), and sodium bicarbonate solution (2x), and is dried ($MgSO_4$). The ether is evaporated to give the crude 4,6-difluoro-αt-methylindanone as an oil which crystallizes on standing. The crude product is purified by flash chromatography on silica-gel, 400 g of J. T. Baker 3405 with petroleum ether-methylene chloride (2:1). Recrystallization from methylene chloride-petroleum ether gives 4,6-difluoro-2-methylindanone, M.P. 68–69° C.

(E) Methyl 5,7-difluoro-2-methylindenyl-3-acetate.

About 20% of a solution containing 4,6-difluoro-2-methylindanone, 15.0 g (83 mmol), and methyl bromoacetate, 14.0 g (1.1 equiv.) in 100 ml dry benzene is added to a stirred suspension of powdered zinc dust (Merck dried 120° C./22 mm.), 6.5 g (1.2 equiv.) in 74 ml dry benzene under a nitrogen atmosphere. Several crystals of iodine are added, and the mixture slowly brought to a reflux. The remainder of the solution is added dropwise over 10 minutes, and the mixture stirred at reflux overnight, i.e., 17 hours. The reaction mixture is cooled to room temperature, and is poured into 2.0 l of 20% aqueous sulfuric acid-crushed ice with stirring. Ether is added until a clear solution is obtained. The ether layer is extracted with 5% aqueous sulfuric acid (3x), water (3x), diluted with methylene chloride and dried ($MgSO_4$). The solvents are evaporated to give crude hydroxy ester.

Powdered phosphorus pentoxide (60.0 g) is added to a solution of the hydroxy ester (20.0 g) in 400 ml of dry benzene. The mixture is refluxed and stirred for 30 minutes. The clear benzene solution is decanted. The residue is rinsed with benzene and then with ether. The combined organic solutions are diluted with ether, extracted six times with aqueous sodium sulfate solution, twice with aqueous potassium bicarbonate solution, diluted with methylene chloride and dried ($MgSO_4$). The crude indenyl acetate product is obtained as an oil when the solvents are evaporated. The product is crystallized from petroleum ether to give methyl 5,7-difluoro-2-methylindenyl-3-acetate, M.P. 69–70° C.

(F) 5,7-difluoro-2-methyl-1-(3,4,5-trimethoxybenzylidene)-3-indenyl acetic acid, a mixture of geometric isomers.

Powdered sodium methoxide, 2.2 g (40 mmol) is added to a suspension of methyl 5,7-difluoro-2-methyl-indenyl-3-acetate (4.78 g) (20 mmol) and 3,4,5-trimethoxybenzaldehyde, 4.32 g (22 mmol), in 40 ml dry methanol under nitrogen. A clear solution results which is refluxed for 60 minutes. An equal volume of water is added, and refluxing continued under nitrogen for 30 minutes to complete saponification. The cold solution is diluted with water and extracted with ether. Nitrogen is bubbled through the aqueous solution to remove the residual ether solvent. Fifty percent aqueous acetic acid (40 ml) is used to precipitate the product. The product is filtered off and washed with water. It is dried in a desiccator over potassium hydroxide pellets, and finally in the oven at 100° C. The crude product is recrystallized to give a mixture of the cis and trans isomers of the acid.

(G) Cis-methyl-5,7-difluoro-2-methyl-1-(3,4,5-trimethoxybenzylidene)-3-indenyl-acetate isolation by column chromatography.

Four drops of concentrated sulfuric acid are added to a solution of 5,7-difluoro-2-methyl-1-(3,4,5-trimethoxybenzylidene)-3-indenyl acetic acid, 1.0 g (2.8 mmol) in 60 ml of dry methanol, and the solution is stirred at reflux overnight. The solution is cooled and crystals separated. They are collected, rinsed with cold methanol-water (1:1) and dried over potassium hydroxide pellets. These crystals are found to be about 95% of the trans-isomer, and could be further purified by recrystallization to give the pure trans-isomer. Water is added to the filtrate from the first crop and a second crop of crystals is obtained. The second crop of crystals is cis-enriched and used for chromatography after it was allowed to react with diazomethane.

1.7 g of cis and trans-mixed esters are chromatographed on a column (3.0×90 cm) of silica-gel, 250 g of J. T. Baker 3405. The column is developed and eluted with halogenated solvents. In this way the trans-isomer and the cis-isomer may be obtained.

(H) Cis-5,7-difluoro-2-methyl-1-(3,4,5-trimethoxybenzylidene)-3-indenyl acetic acid.

0.1 N aqueous sodium hydroxide 3.0 ml (3.0 mmol) is added to cis-methyl 5,7-difluoro-2-methyl-1-(3,4,5-trimethoxybenzylidene)-3-indenylacetate, 266 mg (0.64 mmol) in 20 ml methanol under nitrogen. The mixture is refluxed for 1 hour, cooled, diluted with water and acidified with several ml of 50% acetic acid Crystals form and after further chilling in ice bath, they are collected, washed thoroughly with water and sucked nearly dry. The product is recrystallized, dried over potassium hydroxide pellets in a vacuum desiccator and finally in a vacuum oven at 100C. In this way cis-5,7-difluoro-2-methyl-1-(3,4,5-trimethoxybenzylidene)-3-indenyl acetic acid may be obtained.

(I) cis-5,7-difluoro-2-methyl-1-(3,4,5-trimethoxybenzylidene)-3-(N-benzyl)-indenylacetamide Following the procedures of Example 1(F) and (G) and using the acid described above leads to the formation of the title compound. (R and $R_1$=H, $R_2$=F, $R_3$=H, $R_4$=F, $R_5$, $R_6$ and $R_7$=OCH$_3$, $R_8$=CH$_3$, o=1, M=PhCH$_2$NH)

EXAMPLE 71

α-(1-(3,4,5-Trimethoxybenzylidene)-2-Methyl-5,6-Difluoro-3-Indenyl)-(N-Benzyl)-Propionamide α-[1-(3,4,5-trimethoxybenzylidene)-2-methyl-5,6-difluoro-3-indenyl]-(N-benzyl)-propionamide is prepared following the procedures of Examples 64(A)–(C). (R=H, $R_1$=CH$_3$, $R_2$=H, $R_3$=F, $R_4$=F, $R_5$=$R_6$=$R_7$=OCH$_3$, $R_8$=CH$_3$, o=1, M=PhCH$_2$NH)

EXAMPLE 72

α-(1-(3,4-Trimethoxybenzylidene)-2-Methyl-5-Fluoro-6-Methoxy-3-Indenyl)-(N-Benzyl)-Propionamide α-[1-(3,4,5-trimethoxybenzylidene)-2-methyl-5-fluoro-6-methoxy-3-indenyl]-(N-benzyl)-propionamide is prepared following the procedures of Examples 64(A)–(C). (R=H, $R_1$=CH$_3$, $R_2$=H, $R_3$=F, $R_4$=OCH$_3$, $R_5$=$R_6$=$R_7$=OCH$_3$, $R_8$=CH$_3$, o=1, M=PhCH$_2$NH)

EXAMPLE 73

α-(1-(2,4,6-Trimethoxybenzylidene-2-Methyl-5-Fluoro-3-Indenyl)-(N-Benzyl)-Propionamide α-[1-(2,4,6-trimethoxybenzylidene)-2-methyl-5-fluoro-3-indenyl]-(N-benzyl)-propionamide is prepared following the procedures of Examples 64(A)–(C). (R=H, $R_1$=CH$_3$, $R_2$=H, $R_3$=F, $R_4$=H, $R_5$=R=$R_7$=OCH$_3$, $R_8$=CH$_3$, o=1, M=PhCH$_2$NH)

EXAMPLE 74

(Z)-2-Methyl-1-(3,4,5-Trimethoxybenzylidene-3-(N-Benzyl)-Indenylformamide

Following the procedures of Example 1(E)–(G) and using 3-methylindene-2-carboxylic acid [Beil. 9, 644; Aldrich] leads to the formation of the title compound. (R=$R_1$=do not exist, because o=0; $R_2$=H, $R_3$=H, $R_4$=H, $R_5$=$R_6$=$R_7$=OCH$_3$, $R_8$=CH$_3$, o=0, M=PhCH$_2$NH)

EXAMPLE 75

(Z)-5-Fluoro-2-Methyl-1-(3,4,5-Trimethoxybenzylidene)-3-(N-Benzyl)-Indenylpropionamide (A) (Z)-5-Fluoro-2-methyl-1-(3,4,5-trimethoxybenzylidene)-3-indenylmethyl diazomethyl ketone Diazomethane (excess) in ether (700 ml) is allowed to react with the acid chloride (Example 1(F), 5 g, 12.5 mmol) in CH$_2$Cl$_2$ (100 ml). After 30 min, the solvent was evaporated to give the title compound, which was used in the next step without purification.

(B) (Z)-5-Fluoro-2-methyl-1-(3,4,5-trimethoxybenzylidene)-3-indenylpropionic acid Sodium hydroxide (7 ml, 1M) is added to a solution of silver nitrate (1 g, 5.89 mmol) in water (9 ml). The silver oxide is filtered and is stirred with a solution of (Z)-5-Fluoro-2-methyl-1-(3,4, 5-trimethoxybenzylidene)-3-indenylmethyl diazomethyl ketone (1 g, 2.44 mmol) in ethanol (100 ml) for 3 h under reflux conditions. The solution is filtered. The filtrate is treated with base (2N NaOH, 1 d) and acidified with 2N HCl. The product is extracted with ethyl acetate. The organic phase is washed with water and is dried over Na$_2$SO$_4$. Recrystallization from acetonitrile gives the title compound.

(C) (Z)-5-Fluoro-2-methyl-1-(3,4,5-trimethoxybenzylidene)-3-(N-benzyl)-indenylpropionamide Following the procedure of Example 1(F) and 1(G) and using (Z)-5-fluoro-2-methyl-1-(3,4,5- trimethoxybenzylidene)-3-indenylpropionic acid instead of (Z)-5-fluoro-2-methyl-1-(3,4,5-trimethoxybenzylidene)-3-indenylacetic acid leads to the formation of the title compound. (R=H, $R_1$=H, $R_2$=F, $R_3$=H, $R_4$=H, $R_5$=$R_6$=$R_7$=OCH$_3$, $R_1$=CH$_3$, o=2, M=PhCH$_2$NH)

EXAMPLE 76

(Z)-5-Fluoro-2-Methyl-1-(3,4,5-Trihydroxybenzylidene)-3-(N-Benzyl)-Indenylacetamide BBr$_3$ (4.72 ml, 50 mmol) in CH$_2$Cl$_2$ (30 ml) is added slowly at −78° C. to a solution of (Z)-5-fluoro-2-methyl-1-(3,4,5-trimethoxybenzylidene)-3-(N-benzyl)-indenylacetamide (Example 1(G), 5 g, 10.56 ml) in CH$_2$Cl$_2$ (150 ml). The reaction mixture is stirred at −78° C. for 2 h, then at 25° C. for two days. After cooling, the reaction mixture is poured into the ice-water (200 ml), and is extracted with ethyl acetate. The organic phase is dried (Na$_2$SO$_4$) and is evaporated. The solution of the residue in CH$_3$OH: H$_2$C) (7:3) is chromatographed on reverse phase silica gel to give (Z)-5-fluoro-2-methyl-1-(3,4,5-trihydroxybenzylidene)-3-(N-benzyl)-idenyl acetamide. (R=H, $R_1$=H, $R_2$=F, $R_3$=H, $R_4$=H, $R_5$=$R_6$=$R_7$=OH, $R_8$=CH$_3$, o=1, M=PhCH$_2$NH).

BIOLOGICAL EFFECTS (A) Growth Inhibition

These compounds were assayed for their growth inhibitory activity on the human colon carcinoma cell line, SW-480 obtained from ATCC (Rockville, Md.), to ascertain the degree of growth inhibition. Growth inhibition of this cell line is indicative of a benefit on precancerous lesions and neoplasms. The cell line and growth assay employed for these experiments are well characterized, and are used to evaluate the anti-neoplastic properties of NSAIDs. The assay is used by the United States National Cancer Institute in its screening program for new anti-cancer drugs.

Drug stock solutions were made in 100% DMSO then diluted with RPMI media for cell culture testing. All drug solutions were prepared fresh on the day of testing. The cultured cells were obtained at passage #99 and grown in RPMI media supplemented with 5% fetal calf serum, and 2 mM glutamine, 100 U/ml penicillin, 100 U/ml streptomycin, and 0.25 1µg/ml amphotericin. The cultures were maintained in a humidified atmosphere of 95% air and 5% CO$_2$ at 37° C. The cultures were passaged at preconfluent densities using a solution of 0.05% trypsin and 0.53 mM EDTA. Cells were plated at 1000 cells/well for 96 well flat-bottom microtiter plates.

Tumor cell growth inhibition was assessed using the Sulforhodamine B (SRB) protein binding assay. In this assay, tumor cells were plated in 96-well plates and treated with drug-containing media for six days (continuous exposure). For each plate, 6 wells were designated as no treatment controls, six wells as vehicle (0.1% DMSO) controls, and the remaining wells for drug dilutions with three wells per drug concentration. At the end of the exposure period, the cells were fixed and stained with sulforhodamine B, a protein binding dye. The dye was then solubilized, and the optical density of the resulting solution was determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent inhibition" value then represents the degree of growth inhibition caused by the drug.

For each experiment, an IC$_{50}$ value was determined and used for comparative purposes. This value is equivalent to the concentration of drug needed to inhibit tumor cell growth by 50%. IC$_{50}$ values were obtained graphically by connecting the mean values for each drug concentration tested. Each experiment included at least three wells per drug concentration. Concentration was plotted on a log scale on the X-axis. IC$_{50}$ values obtained for the compounds of different Examples are provided in Table 4 below for the SW-480 cell line.

TABLE 4

| EXAMPLE | IC$_{50}$(µM) |
|---|---|
| 1 | 0.04 |
| 4 | 0.36 |
| 8 | 0.12 |
| 15 | 0.39 |
| 19 | 4.5 |
| 22 | 4.5 |
| 23 | 8.0 |
| 27 | 0.22 |
| 28 | 0.37 |
| 31 | 5.2 |
| 32 | 2.2 |
| 33 | 1.8 |
| 34 | 6.2 |
| 35 | >10 |
| 36 | 3 |
| 37 | >10 |
| 38 | >10 |
| 39 | >10 |
| 40 | >10 |
| 41 | >10 |
| 42 | 0.69 |
| 43 | >10 |
| 44 | >10 |
| 45 | >10 |
| 46 | >10 |
| 47 | 4.1 |
| 48 | 0.5 |
| 51 | 2.25 |
| 55 | 0.5 |
| 57 | 0.26 |
| 58 | 0.98 |

(B) Cyclooxygenase (COX) Inhibition

Compounds of this invention, as well as a positive control, sulindac sulfidewere evaluated to determine whether they inhibited the production of cyclooxygenase (see Table 5 below).

COX catalyzes the formation of prostaglandins and thromboxane by the oxidative metabolism of arachidonic acid. The compounds of this invention were evaluated for inhibitory effects on purified COX The COX was purified from ram seminal vescicles, as described by Boopathy, R. and Balasubramanian, J., 239:371–377, 1988. COX activity was assayed as described by Evans, A. T., et al., "Actions of cannabis constituents on enzymes of arachidonate metabolism anti-inflammatory potential, " Biochem. Pharmacol., 36:2035–2037, 1987. Briefly, purified COX was incubated with achidonic acid (100 µM) for 2.0 min at 37° C. in the presence or absence of test compounds. The assay was terminated by the addition of TCA, and COX activity was determined by absorbance at 530 nm.

TABLE 5

| EXAMPLE | COX I<br>% Inhibition (100 μM)<br>(* - 1000 μm) |
|---|---|
| sulindac sulfide | 86 |
| 1 | <25 |
| 2 | <25 |
| 3 | <25 |
| 4 | <25 |
| 5 | <25 |
| 6 | <25 |
| 7 | <25 |
| 8 | <25 |
| 9 | <25 |
| 10 | <25 |
| 11 | <25 |
| 12 | <25 |
| 13 | <25 |
| 14 | <25 |
| 15 | <25 |
| 16 | <25 |
| 17 | <25 |
| 18 | <25 |
| 19 | 33.3 |
| 20 | 36.5 |
| 21 | 36.5 |
| 22 | <25 |
| 23 | <25 |
| 24 | <25 |
| 25 | 25 |
| 26 | 28.1 |
| 27 | <25 |
| 28 | <25 |
| 29 | <25 |
| 30 | <25 |
| 31 | 30* |
| 32 | 58* |
| 33 | 49* |
| 34 | 31* |
| 35 | 37* |
| 36 | 72* |
| 37 | 38* |
| 38 | 35* |
| 39 | 59* |
| 40 | 34* |
| 41 | 59* |
| 42 | 49* |
| 43 | 36* |
| 44 | 51* |
| 45 | 56* |
| 46 | 98* |
| 47 | 37* |
| 48 | <25 |
| 49 | 25 |
| 50 | 29.2 |
| 51 | <25* |
| 52 | <25 |
| 55 | <25 |
| 57 | <25 |
| 58 | <25 |

(C) Apoptosis

Apoptosis was measured using an assay of cell death based on morphological characteristics of apoptotic cells (i.e., condensed chromatin). Drug preparation and cell culture conditions were the same as for the SRB assay described above, except that HT-29 human colon carcinoma cells were employed. Confluent cultures were established in 12.5 cm² flasks by plating 0.5×10⁶ cells/flask. The cultures were assayed for apoptosis by fluorescent microscopy following labeling with acridine orange and ethidium bromide. Floating and attached cells were collected by trypsinization and washed three times in PBS. One ml aliquots were centrifuged (3 g). The pellet was resuspended in 25 ill media and 1 μl of a dye mixture containing 100 μg/ml acridine orange and 100 μg/ml ethidium bromide prepared in PBS and mixed gently. Ten μl of mixture was placed on a microscope slide and covered with a 22 mm² coverslip and examined under 40× dry objectives using epillumination and filter combination.

An observer blinded to the identity of the treatments scored at least 100 cells per sample. Apoptotic cells were identified by nuclear condensation of chromatin stained by the acridine orange or ethidium bromide. These results are provided in Table 6 below.

TABLE 6

Apoptosis Effects of Compounds

| EXAMPLE | Morphology<br>% Apoptotic Cells<br>(1 μM) | DNA Fragmentation | |
|---|---|---|---|
| | | FS (100 μM) | EC$_{50}$ (μM) |
| 1 | 73 | 4.6 | 0.05 |
| 4 | 68 | 2.4 | 0.25 |
| 8 | 48 | <2 | 0.21 |
| 15 | 72 | 2.1 | 0.3 |
| 19 | <20 | 2 | 7 |
| 22 | 37 | 2.3 | 5 |
| 27 | 71 | 4 | 0.7 |
| 28 | 35 | 2.3 | 0.23 |
| 31 | 30 | <2 | >10 |
| 32 | 55 | 2.5 | 0.32 |
| 33 | 28 | 3.7 | 4 |
| 34 | 45 | 2.1 | >10 |
| 35 | 40 | <2 | >10 |
| 36 | 22 | 5.3 | 0.01 |
| 37 | <20 | 2.5 | >10 |
| 38 | 20 | <2 | >10 |
| 39 | 31 | 2 | >10 |
| 40 | <20 | <2 | >10 |
| 41 | 30 | <2 | >10 |
| 42 | <20 | 3.8 | 3 |
| 43 | 25 | <2 | >10 |
| 44 | 25 | 2.7 | >10 |
| 45 | 40 | 3.4 | >10 |
| 46 | 20 | 4.8 | >10 |
| 47 | 20 | 4.4 | 5.7 |
| 48 | 63 | 2.5 | 0.5 |
| 51 | 40 | <2 | >10 |
| 57 | 73 | <2 | 0.3 |
| 58 | 52 | 2.5 | 0.7 |

Apoptosis was also measured based on the amount of fragmented DNA contained in cell lysates. Briefly, SW-480 colon adenocarcinoma cells were plated in 96-well microtitre plates ("MTP") at a density of 10K cells/well in 180 μl and incubated for 24 hrs. Cells were then treated with 20μl aliquots of appropriately diluted compound, and allowed to incubate for an additional 48 hrs.

After the incubation, samples were prepared according to the following steps. The MTP was centrifuged (15 min., 1000 rpm) and the supernatant was carefully removed by fast inversion of the MTP. The cell pellets in each well were then resuspended in 200 μl lysis buffer and incubated for 45 min. at room temperature to lyse the cells. The lysates were then centrifuged (15 min., 1000 rpm) and 20 μl aliquots of the supernatant (=cytoplasmic fraction) were transferred into the streptavidin coated MTP for analysis. Care was taken not to shake the lysed pellets in the MTP (=cell nucleii containing high molecular weight, unfragmented DNA). Samples were analyzed immediately, because storage at 4 C or −20 C reduces the ELISA-signals. Samples were then processed according to a DNA fragmentation assay protocol, and dose-response curves were generated based on optical density readings. Quantification of DNA was done by a commercially available photometric enzyme-immunoassay manufactured by Mannheim-Boehringer under the name "Cell Death Detection ELISA$^{plus}$". The assay is based on a quantitative sandwich-enzyme-immunoassay-principle using mouse monoclonal antibodies directed against DNA and histones, respectively This allows the specific determination of mono and oligonucleosomes in the cytoplasmatic fraction of cell lysates. In brief, the assay procedure is as follows. The sample (cell-lysate, serum, culture-supernatant etc.) is placed into a streptavidin-coated MTP. Subsequently, a mixture of anti-histone-biotin and anti-DNA-POD are added and incubated for 2 hours. During the incubation period, the anti-histone antibody binds to the histone-component of the nucleosomes and simultaneously fixes the immunocomplex to the streptavidin-coated MTP via its biotinylation. Additionally, the anti-DNA-POD antibody reacts with the DNA component of the nucleosomes. After removal of unbound antibodies by a washing step, the amount of nucleosomes is quantified by the POD retained in the immunocomplex. POD is determined photometrically with ABTS®(2,2'-Azino-di[3-ethyl benzthiazol in-sulfonat])* as substrate.

Fold stimulation (FS=ODmax/ODveh), an indicator of apoptotic response, was determined for each compound tested. $EC_{50}$ values were determined either specifically by data analysis software, or by estimates based on the effective concentration range of each compound (ECR=min. effective dose-min. dose to peak effect). These FS and $EC_{50}$ values for the tested compounds are listed above in Table 6.

The compounds of this invention can be formulated with pharmaceutically acceptable carriers into unit dosage forms in a conventional manner so that the patient in need of therapy for precancerous lesions can periodically (e.g., once or more per day) take a compound according to the method of this invention. The exact initial dose of the compounds of this invention can be determined with reasonable experimentation. One skilled in the art should understand that the initial dosage should be sufficient to achieve a blood plasma concentration approaching a percentage of the $IC_{50}$ value of the compound, with the percentage depending on the chemopreventative or chemotherapeutic indication. The initial dosage calculation would also take into consideration several factors, such as the formulation and mode of administration, e.g. oral or intravenous, of the particular compound. For example, assuming a patient with an average circulatory system volume of about four liters, then based on the reported $IC_{50}$ value for the compound of Example No. 1, one would calculate a dosage of about 0.075 mg of this compound for intravenous administration to achieve a systemic circulatory concentration equivalent to the $IC_{50}$ concentration.

It will be understood that various changes and modifications can be made in the details of procedure, formulation and use without departing from the spirit of the invention, especially as defined in the following claims.

We claim:

1. A pharmaceutical composition comprising a pharmaceutically acceptable carrier and a compound of formula I or pharmaceutically acceptable salt thereof:

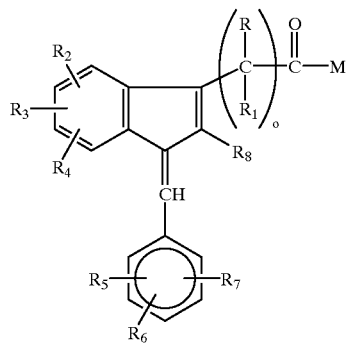

wherein R and $R_1$ are independently selected from the group consisting of hydrogen, hydroxy, lower alkyl and amino; or R and $R_1$ together may be oxygen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are identically selected from the group consisting of hydroxy and lower alkoxy, and the third is selected from the group consisting of hydroxy, halogen, lower alkoxy, lower alkyl, amino and lower dialkylamino; with the proviso that when at least one of $R_2$, $R_3$ or $R_4$ is lower alkoxy, then each of $R_5$, $R_6$ and $R_7$ are hydroxy or lower alkoxy;

$R_8$ is selected from the group consisting of hydrogen and lower alkyl;

o is 0, 1 or 2; and

M is selected from the group consisting of amino, alkylamino, dialkylamino, alkoxyamino, alkenylamino, alkynylamino, hydroxyalkylamino, polyhydroxyalkyl-amino, dialkylaminoalkylamino, aminoalkylamino, benzylamino, anilino, phenylalkylamino, aminoindan, and heterocycloalkylamino where the heterocycles are selected from the group consisting of pyridinyl, piperidinyl, piperazinyl, pyrrollidinyl and N-morpholino; wherein the alkyl between the cyclic structure and the amino may be absent, and the cyclic structures may optionally be substituted with one or more of halo, alkoxy, hydroxy, amino, alkylamino, dialkylamino and sulfonamido.

2. The pharmaceutical composition of claim 1 wherein o is 1 or 2; and

M is selected from the group consisting of amino, alkylamino, dialkylamino, alkenylamino, alkynylamino, hydroxyalkylamino, dialkylaminoalkylamino, arylalkylamino selected from the group consisting of benzylamino, anilino and phenylalkylamino, aminoindan, and heterocycloalkylamino where the heterocycles are selected from the group consisting of pyridinyl, piperidinyl, piperazinyl, and pyrrollidinyl; wherein the alkyl between the cyclic structure and the amino may be absent, and the cyclic structures may optionally be substituted with one or more of halo, alkoxy, hydroxy, amino, alkylamino and dialkylamino.

3. The pharmaceutical composition of claim 2 wherein M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

4. The pharmaceutical composition of claim 3 wherein M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

5. The pharmaceutical composition of claim 4 wherein M is selected from benzylamino and benzylamino substituted with one or more of halo, alkoxy, hydroxy, amino, alkylamino and dialkylamino.

6. The pharmaceutical composition of claim 4 wherein

R and $R_1$ are independently selected from the group consisting of hydrogen and hydroxy; and at least two of $R_5$, $R_6$ and $R_7$ are lower alkoxy and the third is selected from hydroxy, lower alkoxy, amino and lower dialkylamino; or each of $R_5$, $R_6$ and $R_7$ are hydroxy.

7. The pharmaceutical composition of claim 6 wherein

R and $R_1$ are hydrogen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are lower alkoxy and the third is selected from hydroxy and lower alkoxy;

$R_8$ is lower alkyl, o is 1; and

M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkyl amino.

8. The pharmaceutical composition of claim 7 wherein $R_5$, $R_6$ and $R_7$ are each lower alkoxy; and $R_8$ is methyl.

9. The pharmaceutical composition of claim 8 wherein $R_2$ is selected from the group consisting of hydroxy, halogen, lower alkoxy and alkyl mercapto;

$R_4$ is hydrogen; and $R_5$, $R_6$ and $R_7$ are each methoxy.

10. The pharmaceutical composition of claim 9 wherein $R_2$ is selected from the group consisting of hydroxy, halogen and lower alkoxy; and $R_3$ is hydrogen.

11. The pharmaceutical composition of claim 10 wherein $R_2$ is halogen.

12. The pharmaceutical composition of claim 11 wherein $R_2$ is fluoro.

13. The pharmaceutical composition of claim 12 wherein the compound is selected from the group consisting of:

(Z)-5-Fluoro-2-methyl-1-(2,4,6-trimethoxybenzylidene)-3-(N-benzyl)-indenylacetamide;

(Z)-5-Fluoro-2-methyl-1-(3,4,5-trimethoxybenzylidene)-3-(N-benzyl)-indenylacetamide;

(E)-5-Fluoro-2-methyl-1-(3,4,5-trimethoxybenzylidene)-3-(N-benzyl)-indenylacetamide;

(Z)-5-Fluoro-2-methyl-1-(2,3,4-trimethoxybenzylidene)-3-(N-benzyl)-indenylacetamide; and (Z)-5-Fluoro-2-methyl-1-(2,4,5-trimethoxybenzylidene)-3-(N-benzyl)-indenylacetamide.

14. The pharmaceutical composition of claim 13 wherein the compound is (Z)-5-fluoro-2-methyl-1-(3,4,5-trimethoxybenzylidene)-3-(N-benzyl)-indenylacetamide.

15. A method of treating a patient having precancerous lesions comprising administering a pharmacologically effective amount of a compound of formula I or pharmaceutically acceptable salt thereof:

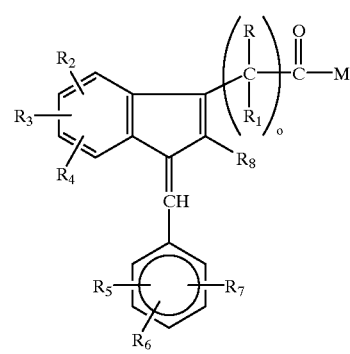

wherein R and $R_1$ are independently selected from the group consisting of hydrogen, hydroxy, lower alkyl and amino; or R and $R_1$ together may be oxygen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are identically selected from the group consisting of hydroxy and lower alkoxy, and the third is selected from the group consisting of hydrogen, hydroxy, halogen, lower alkoxy, lower alkyl, amino and lower dialkylamino; with the proviso that when at least one of $R_2$, $R_3$ or $R_4$ is lower alkoxy, then each of $R_5$, $R_6$ and $R_7$ are hydroxy or lower alkoxy;

$R_8$ is selected from the group consisting of hydrogen and lower alkyl;

o is 0, 1 or 2; and

M is selected from the group consisting of amino, alkylamino, dialkylamino, alkoxyamino, alkenylamino, alkynylamino, hydroxyalkylamino, polyhydroxyalkyl-amino, dialkylaminoalkylamino, aminoalkylamino, benzylamino, anilino, phenylalkylamino, aminoindan, and heterocycloalkylamino where the heterocycles are selected from the group consisting of pyridinyl, piperidinyl, piperazinyl, pyrrollidinyl and N-morpholino; wherein the alkyl between the cyclic structure and the amino may be absent, and the cyclic structures may optionally be substituted with one or more of halo, alkoxy, hydroxy, amino, alkyl amino, dialkylamino and sulfonamido.

16. The method of claim 15 wherein o is 1 or 2; and

M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

17. The method of claim 16 wherein M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

18. The method of claim 17 wherein M is selected from benzylamino and benzylamino substituted with one or more of halo, alkoxy, hydroxy, amino, alkylamino and dialkylamino.

19. The method of claim 17 wherein

R and $R_1$ are independently selected from the group consisting of hydrogen and hydroxy; and at least two of $R_5$, $R_6$ and $R_7$ are lower alkoxy and the third is selected from hydroxy, lower alkoxy, amino and lower dialkylamino; or each of $R_5$, $R_6$ and $R_7$ are hydroxy.

20. The method of claim 19 wherein

R and $R_1$ are hydrogen, $R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are lower alkoxy and the third is selected from hydroxy and lower alkoxy;

$R_8$ is lower alkyl;

o is 1; and

M is selected from the group consisting of alkenylamino, alkynylamino, benzylamino, and pyridinylalkylamino, wherein the cyclic structures may optionally be substituted with one or more of halo, alkoxy, hydroxy, amino, alkylamino and dialkylamino.

21. The method of claim 20 wherein $R_5$, $R_6$ and $R_7$ are each lower alkoxy; and $R_8$ is methyl.

22. The method of claim 21 wherein $R_2$ is selected from the group consisting of hydroxy, halogen, lower alkoxy and alkyl mercapto;

$R_4$ is hydrogen; and $R_5$, $R_6$ and $R_7$ are each methoxy.

23. The method of claim 22 wherein $R_2$ is selected from the group consisting of hydroxy, halogen and lower alkoxy; and $R_3$ is hydrogen.

24. The method of claim 23 wherein $R_2$ is fluoro.

25. The method of claim 24 wherein the compound is selected from the group consisting of:

(Z)-5-Fluoro-2-methyl-1-(2,4,6-trimethoxybenzylidene)-3-(N-benzyl)-indenylacetamide;

(Z)-5-Fluoro-2-methyl-1-(3,4,5-trimethoxybenzylidene)-3-(N-benzyl)-indenylacetamide;

(Z)-5-Fluoro-2-methyl-1-(2,3,4-trimethoxybenzylidene)-3-(N-benzyl)-indenylacetamide; and (Z)-5-Fluoro-2-methyl-1-(2,4,5-trimethoxybenzylidene)-3-(N-benzyl)-indenylacetamide.

26. The method of claim 25 wherein the compound is (Z)-5-fluoro-2-methyl-1-(3,4,5-trimethoxybenzylidene)-3-(N-benzyl)-indenylacetamide.

27. A method for inhibiting the growth of neoplastic cells comprising exposing the cells to a growth inhibiting effective amount of a compound of formula I or pharmaceutically acceptable salt thereof:

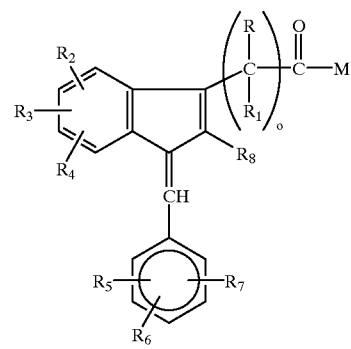

wherein R and $R_1$ are independently selected from the group consisting of hydrogen, hydroxy, lower alkyl and amino; or R and $R_1$ together may be oxygen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are identically selected from the group consisting of hydroxy and lower alkoxy, and the third is selected from the group consisting of hydrogen, hydroxy, halogen, lower alkoxy, lower alkyl, amino and lower dialkylamino; with the proviso that when at least one of $R_2$, $R_3$ or $R_4$ is lower alkoxy, then each of $R_5$, $R_6$ and $R_7$ are hydroxy or lower alkoxy;

$R_8$ is selected from the group consisting of hydrogen and lower alkyl;

o is 0, 1 or 2; and

M is selected from the group consisting of amino, alkylamino, dialkylamino, alkoxyamino, alkenylamino, alkynylamino, hydroxyalkylamino, polyhydroxyalkyl-amino, dialkylaminoalkylamino, aminoalkylamino, benzylamino, anilino, phenylalkylamino, aminoindan, and heterocycloalkylamino where the heterocycles are selected from the group consisting of pyridinyl, piperidinyl, piperazinyl, pyrrollidinyl and N-morpholino; wherein the alkyl between the cyclic structure and the amino may be absent, and the cyclic structures may optionally be substituted with one or more of halo, alkoxy, hydroxy, amino, alkylamino, dialkylamino and sulfonamido.

28. The method of claim 27 wherein o is 1 or 2; and

M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

29. The method of claim 28 wherein M is selected from the group consisting of alkenylamino, alkynylamino, benzylamino, and pyridinylalkylamino, wherein the cyclic structures may optionally be substituted with one or more of halo, alkoxy, hydroxy, amino, alkylamino and dialkylamino.

30. The method of claim 29 wherein M is selected from benzylamino and benzylamino substituted with one or more of halo, alkoxy, hydroxy, amino, alkylamino and dialkylamino.

31. The method of claim 29 wherein

R and $R_1$ are independently selected from the group consisting of hydrogen and hydroxy; and at least two of $R_5$, $R_6$ and $R_7$ are lower alkoxy and the third is selected from hydroxy, lower alkoxy, amino and lower dialkylamino; or each of $R_5$, $R_6$ and $R_7$ are hydroxy.

32. The method of claim 31 wherein

R and $R_1$ are hydrogen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are lower alkoxy and the third is selected from hydroxy and lower alkoxy;

$R_8$ is lower alkyl o is 1; and

M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkyl amino.

33. The method of claim 32 wherein $R_5$, $R_6$ and $R_7$ are each lower alkoxy; and $R_8$ is methyl.

34. The method of claim 33 wherein $R_2$ is selected from the group consisting of hydroxy, halogen, lower alkoxy and alkyl mercapto;

$R_4$ is hydrogen; and $R_5$, $R_6$ and $R_7$ are each methoxy.

35. The method of claim 34 wherein $R_2$ is selected from the group consisting of hydroxy, halogen and lower alkoxy; and $R_3$ is hydrogen.

36. The method of claim 35 wherein $R_2$ is halogen.

37. The method of claim 36 wherein the compound is (Z)-5-fluoro-2-methyl-1-(3,4,5-trimethoxybenzylidene)-3-(N-benzyl)-indenylacetamide.

38. A method for regulating apoptosis in human cells comprising exposing said cells to an effective amount of a compound of the formula:

I wherein R and $R_1$ are independently selected from the group consisting of hydrogen, hydroxy, lower alkyl and amino; or R and $R_1$ together may be oxygen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are identically selected from the group consisting of hydroxy and lower alkoxy, and the third is selected from the group consisting of hydrogen, hydroxy, halogen, lower alkoxy, lower alkyl, amino and lower dialkylamino; with the proviso that when at least one of $R_2$, $R_3$ or $R_4$ is lower alkoxy, then each of $R_5$, $R_6$ and $R_7$ are hydroxy or lower alkoxy;

$R_8$ is selected from the group consisting of hydrogen and lower alkyl;

o is 0, 1 or 2; and

M is selected from the group consisting of amino, alkylamino, dialkylamino, alkoxyamino, alkenylamino, alkynylamino, hydroxyalkylamino, polyhydroxyalkyl-amino, dialkylaminoalkylamino, aminoalkylamino, benzylamino, anilino, phenylalkylamino, aminoindan, and heterocycloalkylamino where the heterocycles are selected from the group consisting of pyridinyl, piperidinyl, piperazinyl, pyrrollidinyl and N-morpholino; wherein the alkyl between the cyclic structure and the amino may be absent, and the cyclic structures may optionally be substituted with one or more of halo, alkoxy, hydroxy, amino, alkylamino, dialkylamino and sulfonamido.

39. The method of claim 38 wherein o is 1 or 2; and

M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

40. The method of claim 39 wherein M is selected from the group consisting of alkenylamino, alkynylamino, benzylamino, and pyridinylalkylamino; wherein the cyclic structures may optionally be substituted with one or more of halo, alkoxy, hydroxy, amino, alkylamino and dialkylamino.

41. The method of claim 40 wherein M is selected from benzylamino and benzylamino substituted with one or more of halo, alkoxy, hydroxy, amino, alkylamino and dialkylamino.

42. The method of claim 40 wherein

R and $R_1$ are independently selected from the group consisting of hydrogen and hydroxy; and at least two of $R_5$, $R_6$ and $R_7$ are lower alkoxy and the third is selected from hydroxy, lower alkoxy, amino and lower dialkylamino; or each of $R_5$, $R_6$ and $R_7$ are hydroxy.

43. The method of claim 42 wherein

R and $R_1$ are hydrogen;

$R_2$, $R_3$ and $R_4$ are independently selected from the group consisting of hydrogen, hydroxy, halogen, lower alkoxy, lower alkyl and alkyl mercapto;

at least two of $R_5$, $R_6$ and $R_7$ are lower alkoxy and the third is selected from hydroxy and lower alkoxy;

$R_8$ is lower alkyl;

o is 1; and

M is selected from the group consisting of alkenylamino, alkynylamino, benzylamino, and pyridinylalkylamino; wherein the cyclic structures may optionally be substituted with one or more of halo, alkoxy, hydroxy, amino, alkyl amino and dialkylamino.

44. The method of claim 43 wherein $R_5$, $R_6$ and $R_7$ are each lower alkoxy; and $R_8$ is methyl.

45. The method of claim 44 wherein $R_2$ is selected from the group consisting of hydroxy, halogen, lower alkoxy and alkyl mercapto;

$R_4$ is hydrogen; and $R_5$, $R_6$ and $R_7$ are each methoxy.

46. The method, of claim 45 wherein $R_2$ is selected from the group consisting of hydroxy, halogen and lower alkoxy, and $R_3$ is hydrogen.

47. The method of claim 46 wherein $R_2$ is fluoro.

* * * * *